(12) United States Patent
Bublewitz et al.

(10) Patent No.: US 7,902,269 B2
(45) Date of Patent: *Mar. 8, 2011

(54) DENTAL MATERIAL BASED ON ALKOXYSILYL-FUNCTIONAL POLYETHERS CONTAINING A SALT OF A STRONG BASE AS CATALYST

(75) Inventors: Alexander Bublewitz, Herborn (DE); Jens-Peter Reber, Meinerzhagen (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 653 days.

This patent is subject to a terminal disclaimer.

(21) Appl. No.: 10/589,329

(22) PCT Filed: Feb. 14, 2005

(86) PCT No.: PCT/EP2005/001470
§ 371 (c)(1),
(2), (4) Date: Aug. 14, 2006

(87) PCT Pub. No.: WO2005/077321
PCT Pub. Date: Aug. 25, 2005

(65) Prior Publication Data
US 2007/0173557 A1 Jul. 26, 2007

(30) Foreign Application Priority Data
Feb. 13, 2004 (DE) .......................... 10 2004 008 022

(51) Int. Cl.
*A61K 6/10* (2006.01)
*C08G 77/08* (2006.01)
*A61C 9/00* (2006.01)

(52) U.S. Cl. .............. 523/109; 528/20; 528/21; 433/214

(58) Field of Classification Search .................. 523/109; 528/20, 21; 433/214
See application file for complete search history.

(56) References Cited

U.S. PATENT DOCUMENTS

| | | | |
|---|---|---|---|
| 3,082,527 A | 3/1963 | Nitzsche et al. | |
| 3,127,363 A | 3/1964 | Nitzsche et al. | |
| 3,825,618 A | 7/1974 | Pepe | |
| 4,160,778 A | 7/1979 | Hildon et al. | |
| 4,174,338 A | 11/1979 | Goller et al. | |
| 4,362,885 A * | 12/1982 | Panster et al. | 556/446 |
| 4,375,549 A * | 3/1983 | Renga | 556/470 |
| 4,798,878 A | 1/1989 | Brinkmann et al. | |
| 4,906,707 A | 3/1990 | Yukimoto et al. | |
| 5,086,148 A | 2/1992 | Jochum et al. | |
| 5,118,290 A | 6/1992 | Müller et al. | |
| 5,249,862 A | 10/1993 | Herold et al. | |
| 5,286,105 A | 2/1994 | Herold et al. | |
| 5,304,621 A * | 4/1994 | Staiger et al. | 528/12 |
| 5,332,122 A | 7/1994 | Herold et al. | |
| 5,623,030 A | 4/1997 | Tsumura et al. | |
| 5,739,245 A | 4/1998 | Lubbers et al. | |
| 5,916,981 A | 6/1999 | Cifuentes et al. | |
| 5,925,723 A | 7/1999 | Friebe et al. | |
| 6,077,896 A * | 6/2000 | Yano et al. | 524/308 |
| 6,124,235 A | 9/2000 | Letoffe et al. | |
| 6,129,244 A | 10/2000 | Hörth | |
| 6,218,461 B1 * | 4/2001 | Schwabe et al. | 524/588 |
| 6,310,170 B1 | 10/2001 | Johnston et al. | |
| 6,503,994 B1 | 1/2003 | Nehren et al. | |
| 6,599,974 B1 | 7/2003 | Bublewitz et al. | |
| 6,884,852 B1 | 4/2005 | Klauck et al. | |
| 2002/0086942 A1 | 7/2002 | Fujita et al. | |
| 2002/0156149 A1 | 10/2002 | Schaub et al. | |
| 2002/0156186 A1 * | 10/2002 | Bublewitz et al. | 525/100 |
| 2003/0083399 A1 | 5/2003 | Schaub et al. | |
| 2003/0158275 A1 | 8/2003 | McClelland et al. | |
| 2004/0042960 A1 | 3/2004 | Frey et al. | |
| 2004/0048998 A1 | 3/2004 | Klein et al. | |
| 2004/0146713 A1 | 7/2004 | Schaub et al. | |
| 2004/0181025 A1 | 9/2004 | Schindler et al. | |
| 2005/0250871 A1 | 11/2005 | Bublewitz et al. | |
| 2005/0260401 A1 * | 11/2005 | Bachon et al. | 428/317.7 |

FOREIGN PATENT DOCUMENTS

| | | |
|---|---|---|
| DE | 11 63 021 | 2/1964 |
| DE | 19 59 842 | 9/1970 |
| DE | 26 44 193 | 4/1978 |
| DE | 44 39 769 | 5/1996 |
| DE | 100 61 195 | 6/2002 |

(Continued)

OTHER PUBLICATIONS

International Search Report in English, Feb. 2007.
Schriftenreihe Pigmente Degussa Kieselsäuren [Publication Series Pigments Degussa Silicas], No. 12, p. 5, as well as No. 13, p. 3.
Ullmann's Encyclopedia of Industrial Chemistry, vol. 21, p. 523.
ZM 93 (Zahnmedizin)(2003) No. 15, p. 32.
Source: http://www.cem.msu.edu/~reusch/VirtualText/suppmnt2.htm Molecular Structure and Acidity, pp. 1-13.
Source: http://ww.tgs-chemie.de/pks-wert.htm.
Source: Y. Chiang, E.B. Whipple, J. Am. Chem. Soc., 1963, vol. 85 2763-2767.

(Continued)

*Primary Examiner* — Tae H Yoon
(74) *Attorney, Agent, or Firm* — Collard & Roe, P.C.

(57) ABSTRACT

The invention relates to condensation cross-linked dental materials based on alkoxysilyl-functional polyethers and at least one catalyst, the catalyst consisting of a salt and at least one anion of a saturated and/or unsaturated (cyclo)aliphatic carboxylic acid. The salt is formed from at least one cation selected from the group consisting of: complexes of alkali metal cations or ammonium cations and crown ethers and/or cryptands; tetraalkyl-, tetraaryl-, trialkylaryl-, dialkyldiaryl-, and monoalkyltriaryl-ammonium cations, tetraalkyl-, tetraaryl-, trialkylaryl-, dialkyldiaryl-, and monoalkyltriaryl-phosphonium cations, tetraalkyl-, and monoalkyltriaryl-stibonium cations; cations formed by the protonation of a base with a $pK_{BH+}$ value of at least 20, measured in acetonitrile; and combinations of the complexes and cations. The carboxylic acid is a branched carboxylic acid, whose alkyl chain that is provided on the carboxyl group has a length of at least 2 carbon atoms or an unbranched carboxylic acid, whose alkyl chain that is provided on the carboxyl group has a length of at least 4 carbon atoms.

13 Claims, No Drawings

FOREIGN PATENT DOCUMENTS

| | | |
|---|---|---|
| DE | 101 04 079 | 8/2002 |
| DE | 101 39 132 | 2/2003 |
| EP | 0 269 819 A2 | 6/1988 |
| EP | 0 170 865 | 7/1989 |
| EP | 0 372 561 | 6/1990 |
| EP | 0 492 413 | 11/1994 |
| EP | 0 492 412 | 3/1995 |
| EP | 0 723 807 | 7/1996 |
| EP | 0 748 621 | 12/1996 |
| EP | 0 950 908 | 10/1999 |
| EP | 0 541 972 | 9/2000 |
| EP | 1 081 191 A | 3/2001 |
| EP | 1 226 808 A | 7/2002 |
| EP | 1 402 873 A | 3/2004 |
| WO | WO 98/44860 | 10/1998 |
| WO | WO 99/18912 | 4/1999 |
| WO | WO 99/48942 | 9/1999 |
| WO | WO 01/12237 | 2/2001 |
| WO | WO 02/08323 | 1/2002 |
| WO | WO 02/45661 | 6/2002 |
| WO | WO 2005/077321 | 8/2005 |

OTHER PUBLICATIONS

Source: http://www.zirchrom.com/organic.htm, Dissociation Constants of Organic Acids and Bases, pp. 1-14.

Source: W.C. Davies, H.W. Addis, J. Chem. Soc., 1937, 1622-1629.

* cited by examiner

DENTAL MATERIAL BASED ON ALKOXYSILYL-FUNCTIONAL POLYETHERS CONTAINING A SALT OF A STRONG BASE AS CATALYST

CROSS REFERENCE TO RELATED APPLICATIONS

Applicants claim priority under 35 U.S.C. §119 of German Application No. 10 2004 008 022.4 filed Feb. 13, 2004. Applicants also claim priority under 35 U.S.C. §365 of PCT/EP2005/001470 filed Feb. 14, 2005. The international application under PCT article 21(2) was not published in English.

This invention relates to condensation-crosslinked dental materials, particularly condensation-crosslinked two-component dental impression materials based on alkoxysilyl-functional polyethers, which are especially suitable for taking impressions, and their use. Such materials are used in dentistry, for example for taking tooth impressions, bite registration, denture rebasing, as temporary and permanent dental cement, temporary closure material, or dental prosthodontic material.

Known condensation-crosslinking dental materials ordinarily contain hydroxy-functional polymers with a silicone backbone that harden in the presence of tin compounds as catalysts, alkoxysilanes and/or silicate esters as crosslinkers, and water. Of course such materials are relatively hydrophobic because of the silicone backbone of the polymers, so that substantial proportions of surfactants have to be added to them to reduce surface tension and to establish the necessary wettability. Another drawback of these compositions is the use of toxicologically objectionable organic tin compounds as catalysts.

Alternatively to these, two-component dental materials are known that contain polymers having terminal alkoxysilyl groups with a hydrophilic polyether backbone, which have adequately hydrophilic properties for wetting the moist dental substance. These materials usually consist of a base component containing an alkoxysilyl-functional polyether with an average molecular weight of 800 to 20,000 g/mole, which may also have synthetically derived urea and/or urethane groups, fillers and optionally other additives, and a catalyst component that contains an organic and/or inorganic acid as catalyst.

EP 0 269 819 B1 discloses condensation-crosslinking two-component dental materials whose base components contain polyaddition products containing alkoxysilyl end groups with a predominantly linear molecular structure and an average molecular weight of 800 to 20,000 g/mol, which contain 25 to 90 wt. % polyether groups, 0.5 to 10 wt. % urethane groups, 0.5 to 10 wt. % urea groups, and 1 to 25 wt. % alkoxysilyl groups, and whose catalyst components have a mixture containing water and organic and/or inorganic acids in ratios by weight of 1:0.01 to 1:40 (water/acid). Of course the synthesis of the functional polyether polymers contained in the base component is very tedious and costly. Another drawback of these dental materials is their use of catalysts containing acid. On the one hand, the oral mucosa and the dental enamel may be damaged when taking the impression in the patient's mouth. Furthermore, these systems permit no addition of substances containing nitrogen bases such as astringents, for example epinephrine, or other acid-labile therapeutic additives, since they are inactivated by the acid catalyst because of protonation or cleavage. The use of acids in the production of the dental materials also requires appropriate safety precautions.

EP 1 226 808 A2 discloses condensation-crosslinking two-component dental materials consisting of a base component and a catalyst component whose base components contain alkoxysilyl-functional polyethers with linear or branched main chains and an average molecular weight of 800 to 20,000 g/mol, which contain 20 to 95 wt. % polyether groups, 0.2 to 25 wt. % terminal alkoxysilyl groups, up to 10 wt. % urethane groups or urea groups, and whose catalyst components have a mixture containing water and organic and/or inorganic acid in a ratio by weight of 1:0.01 to 1:40. The catalyst component preferably contains p-toluenesulfonic acid hydrate as catalyst and a polyether diol and other additives such as fillers, paraffin, emulsifier, and the like. The functional polyether polymers used in these dental materials are in fact simpler and more economical to synthesize than those mentioned above, and are distinguished by better kinetics of setting. Of course these dental materials also make use of catalysts containing acid, so that on the one hand there is a risk of damaging the oral mucosa and the dental enamel when taking the impression in the patient's mouth, and furthermore no acid-labile therapeutic additives can be added. Another drawback of the systems is their lower storage stability. Of course a setting time that is independent of the time of storage is one of the most important requirements for a dental impression material.

To crosslink polyurethanes that have polyether groups to be used as adhesives or sealants, WO 99/48942 proposes using metal-organic compounds such as iron or tin compounds, for example tin(II) octanoate, or tertiary amines such as triethylamine. However, their high toxicity is a drawback to these catalysts, so that suitable safety precautions have to be taken in the production of the material, and the materials cannot be used directly as dental impression compositions. Furthermore, tertiary amines especially are odor-intensive so that their use in dental materials is undesirable. Also, the polyurethanes used in these materials are characterized by strong intermolecular interactions because of their high proportion of urethane groups, which leads to elevated viscosity of the materials with a given molecular chain length compared to alkoxysilyl-function polyethers, for which reason less filler can be used in these materials, which in turn causes high production costs.

It is therefore the purpose of this invention to make available a hydrophilic condensation-crosslinking dental material, especially a condensation-crosslinking two-component dental impression material, based on alkoxysilyl polyethers, that is stable in storage, and in particular promises constant reaction kinetics even after at least 18 months of storage, that has good biocompatibility, and especially has neutral odor and taste, and also permits the addition of acid-labile additives such as astringents containing nitrogen, medications, bactericides, fungicides, and the like, and has ingredients that are as toxicologically harmless as possible.

This task is accomplished according to the invention by a condensation-crosslinking dental material with the composition according to Patent claim 1.

Surprisingly, we found in the course of this invention that the salt catalysts to be used according to the invention have good catalytic activity for condensation reactions and they are therefore outstandingly suitable for use as catalysts in condensation-crosslinking dental materials based on alkoxysilyl-functional polyethers. The dental materials pursuant to the invention have not only reaction kinetics suitable for dental materials, but in particular they also have processing and setting times that are proper in practice. These catalysts are distinguished from the substances known up to now for this purpose, such as metal-organic compounds and tertiary amines, by good biocompatibility, and require fewer rigid safety precautions in the production of the dental materials. In particular, the use of catalysts containing heavy metals such as tin-, zinc-, or lead-organic catalyst compounds can be omitted. Another advantage of the salt catalysts used according to the invention compared to the primary, secondary, and tertiary amines known in the state of the art is their odor and taste neutrality, which is an important property for a dental impression material, to achieve patient acceptance and to avoid retching by the patient during its application. In addition, it was unexpected for one skilled in the art that such dental materials have reaction kinetics that stay the same even after months of storage, in particular constant processing and setting times. This results in part from the fact that catalyst salts used in accordance with the invention undergo no side reactions or degradation reactions with other ingredients, for example, with the fillers, with the polyethers that may be used as paste-formers, or with the alkoxysilyl polyethers, during storage or after hardening. Aside from this, the use of a salt as catalyst is also advantageous compared to the use of a free acid or a free base such as a tertiary amine because the salt has a moderate pH, which provides for good compatibility of the dental materials according to the invention with the oral mucosa and with the dental enamel, so that no etching or irritation occurs during its application. Another advantage of the dental materials according to the invention lies in the fact that acid-labile additives, particularly astringents containing nitrogen, medications, bactericides, fungicides, and the like can also be added to them without their being degraded during storage.

The dental materials pursuant to the invention can be formulated either as one-component dental materials or as two-component dental materials. While the formulation of the one-component dental materials has to be as absolutely anhydrous as possible, to prevent a reaction of the alkoxysilyl-functional polyethers during storage, and the reaction of the alkoxysilyl-functional polyethers after application of the materials to the object to be copied is initiated by atmospheric moisture, water is preferably added to the catalyst component of the two-component dental material according to the invention. It is preferred for the two-component dental materials pursuant to the invention to be formulated so that base component A contains
   a) at least one alkoxysilyl-functional polyether,
and catalyst component B contains
   b) at least one catalyst and
   c) water,
with at least one catalyst b) being a salt that is formed from at least one cation selected from the group consisting of
   complexes of alkali metal or ammonium cations with crown ethers and/or cryptands,
   tetraalkyl-, tetraaryl-trialkylaryl-, dialkyldiaryl-, monoalkyltriarylammonium cations, tetraalkyl-, tetraaryl-, trialkylaryl-, dialkyldiaryl-, monoalkyltriarylphosphonium cations, tetraalkyl-, tetraaryl-trialkylaryl-, dialkyldiaryl-, monoalkyltriarylarsonium cations, tetraalkyl-, tetraaryl-trialkylaryl-, dialkyldiaryl-, monoalkyltriarylstibonium cations,
   cations formed by protonation of a base with a $pK_{BH+}$ value of at least 20 measured in acetonitrile
and combinations thereof and at least one anion of a saturated and/or unsaturated (cyclo)aliphatic carboxylic acid, with the carboxylic acid being a branched carboxylic acid with the length of the (cyclo)alkyl chain provided on the carboxyl group being at least 2 carbon atoms, or an unbranched carboxylic acid with the length of the (cyclo)alkyl chain provided on the carboxyl group being at least 4 carbon atoms. Independently of formulation as a one- or two-component material, the anion of the catalyst salt to be used pursuant to the invention is preferably an anion of a branched carboxylic acid with the length of the (cyclo)alkyl chain provided on the carboxyl group being at least 3 carbon atoms, very preferably at least 4, and most preferably at least 5 carbon atoms, or an unbranched carboxylic acid with the length of the (cyclo)alkyl chain provided on the carboxyl group being at least 5 carbon atoms, with anions of appropriate (cyclo)aliphatic monocarboxylic acids being especially preferred.

According to a first preferred embodiment of this invention, the catalyst b) used is at least one salt formed from at least one crown ether-alkali metal ion complex, crown ether-ammonium ion complex, cryptand-alkali metal ion complex, and/or cryptand-ammonium ion complex, and at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms.

In this embodiment, the cation of the catalyst salt used preferably is a complex formed from one or more lithium, sodium, potassium, rubidium, cesium, and/or ammonium ions and one or more of the following crown ethers and/or cryptands:

15-Crown-5, 18-crown-6, dibenzo-18-crown-6, dibenzo-21-crown-7, dibenzo-24-crown-8, dibenzo-30-crown-10, 1,4,10-trioxa-7,13-diazacyclopentadecane, 4,7,13,18-tetraoxa-1,10-diazabicyclo[8.5.5]eicosane, 1,4,10,13-tetraoxa-7,16-diazacyclooctadecane, 3,6,9,14-tetrathiabicyclo[9.2.1]tetradeca-11,13-diene, 1,4,7,10-tetrathiacyclododecane, 1,5,9,13-tetrathiacyclohexadecane-3,11-diol, 1,5,9-triazacyclododecane, 1,4,7-triazacyclononane, 1,4,7,10,13,16-hexamethyl-1,4,7,10,13,16-hexaazacyclooctadecane,

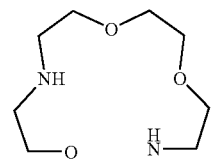

1,4,10-Trioxa-7, 13-diaza-cyclopentadecane

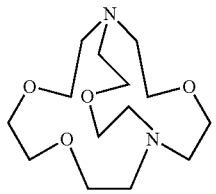

4,7,13,18-Tetraoxa-1,10-diazabicyclo[8.5.5]eicosane

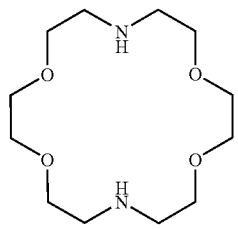

1,4,10,13-Tetraoxa-7,16-diazacyclooctadecane

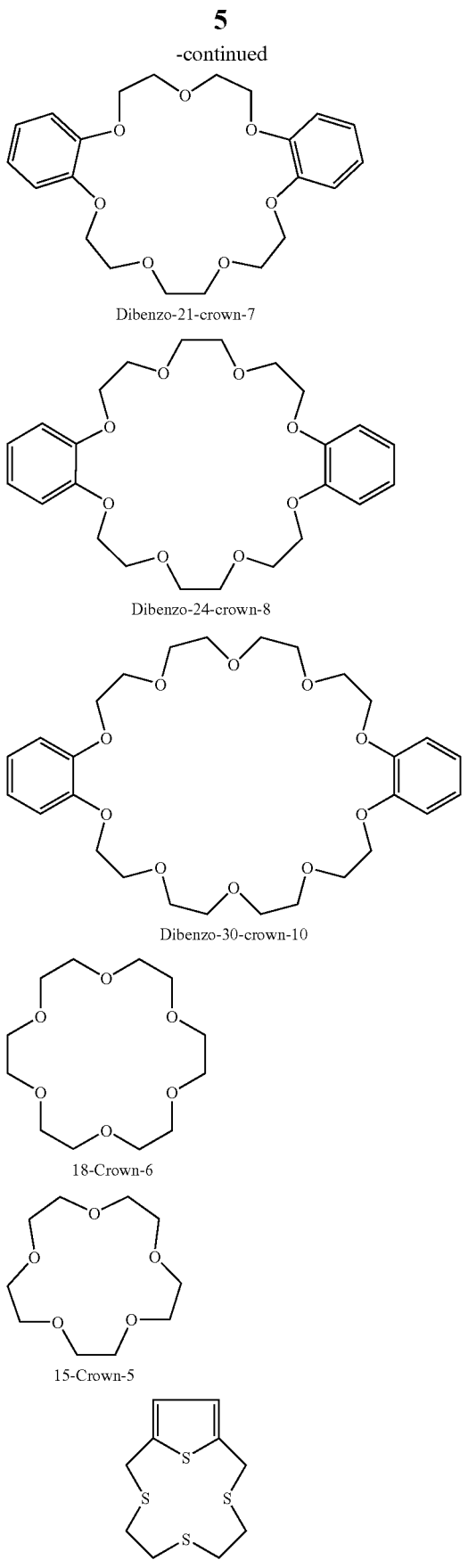

Dibenzo-21-crown-7

Dibenzo-24-crown-8

Dibenzo-30-crown-10

18-Crown-6

15-Crown-5

3,6,9,14-Tetrathiabicyclo[9.2.1]tetradeca-11,13-diene

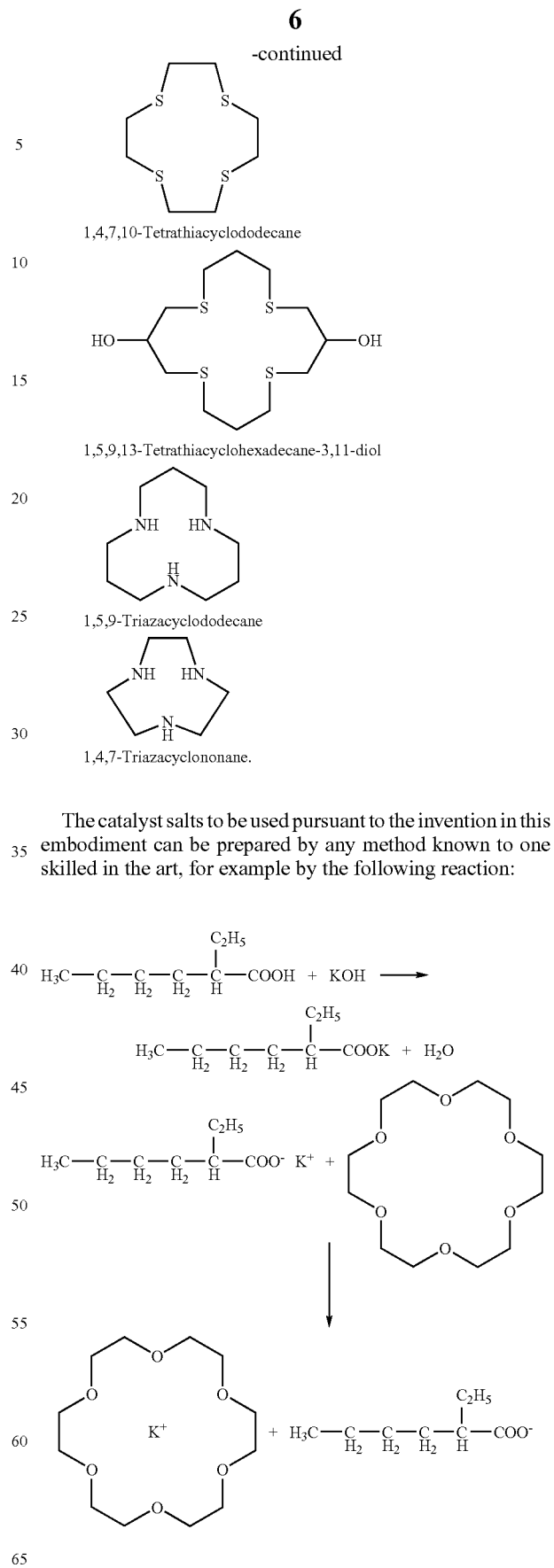

1,4,7,10-Tetrathiacyclododecane 1,5,9,13-Tetrathiacyclohexadecane-3,11-diol 1,5,9-Triazacyclododecane 1,4,7-Triazacyclononane.

The catalyst salts to be used pursuant to the invention in this embodiment can be prepared by any method known to one skilled in the art, for example by the following reaction:

According to a second preferred embodiment of this invention, the catalyst b) used is at least one salt from at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms, and a tetraalkyl-, tetraaryl-, trialkylaryl-, dialkyldiaryl-, monoalkyltriarylammonium, tetraalkyl-, tetraaryl-, trialkylaryl-, dialkyldiaryl-, monoalkyltriarylphosphonium, tetraalkyl-, tetraaryl-, trialkylaryl-, dialkyldiaryl-, monoalkyltriarylarsonium, tetraalkyl-, tetraaryl-, trialkylaryl-, dialkyldiaryl-, and/or monoalkyltriarylstibonium cation. Examples of suitable cations for the catalyst salts to be used according to this embodiment are tetramethylammonium, tetraethylammonium, tetrapropylammonium, tetrabutylammonium, tetrapentylammonium, tetrahexylammonium, tetraheptylammonium, tetraoctylammonium, tetranonylammonium, tetradecylammonium, Tetramethylphosphonium, tetraethylphosphonium, tetrapropyl-phosphonium, tetrabutylphosphonium, tetrapentylphosphonium, tetrahexylphosphonium, tetraheptylphosphonium, tetraoctylphosphonium, tetranonylphosphonium, tetradecylphosphonium, tetramethylarsonium, tetraethylarsonium, tetrapropylarsonium, tetrabutylarsonium, tetrapentylarsonium, tetrahexylarsonium, tetraheptylarsonium, tetraoctylarsonium, tetranonylarsonium, tetradecylarsonium, tetramethylstibonium, tetraethylstibonium, tetrapropylstibonium, tetrabutylstibonium, tetrapentylstibonium, tetrahexylstibonium, tetraheptylstibonium, tetraoctylstibonium, tetranonylstibonium, tetradecylstibonium, lauryltrimethylammonium, myristyltrimethylammonium, cetyltrimethylammonium, stearyltrimethylammonium, lauralkonium, myristalkonium, cetalkonium, stearalkonium, cetylethyldimethylammonium, benzyltriethylammonium, and benzalkonium ions.

The salts of the aforementioned carboxylate anions and the alkyl- and/or aryl-substituted ammonium, phosphonium, arsonium, or stibonium ions according to this form of embodiment can be prepared by any method known to one skilled in the art, with the following synthesis having proved to be particularly suitable, for example:

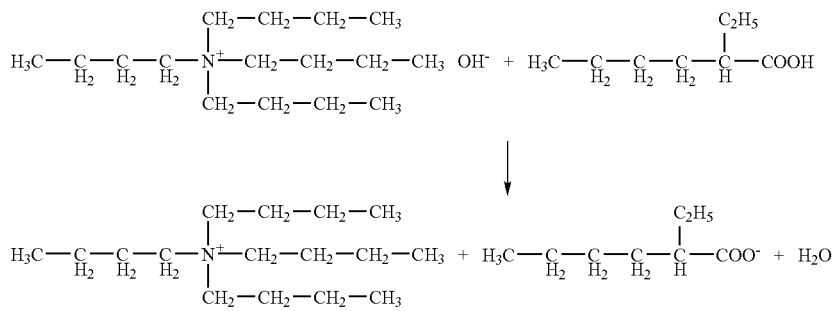

According to a third preferred embodiment of this invention, the catalyst b) used is at least one salt formed from at least one anion of a saturated and/or unsaturated (cyclo)aliphatic carboxylic acid, with the carboxylic acid being a branched carboxylic acid with a length of the (cyclo)alkyl chain provided on the carboxyl group of at least 2 carbon atoms, or an unbranched carboxylic acid with a length of the (cyclo)alkyl chain provided on the carboxyl group of at least 4 carbon atoms and a cation formed by the protonation of a base with a $pK_{BH+}$ value of at least 20 measured in acetonitrile. Especially good results are obtained when the dental material contains as catalyst b) a salt formed from an afore-mentioned anion and a cation formed by protonation of a base with a $pK_{BH+}$ value of at least 21, with special preference 22, and very particularly preferably 23 measured in acetonitrile.

In furtherance of the concept of the invention, it is proposed in the third embodiment of this invention to use as catalyst b) a salt formed from an anion of one of the aforementioned carboxylic acids and a protonated base, with the base having a structure that allows mesomeric stabilization of the positive charge after protonation of the base. Mesomeric stabilization in the context of this invention, in agreement with general textbook knowledge, means that at least two limiting structures can be drawn for the protonated base in which the positive charge is localized on different atoms, and that π-electrons are delocalized in the protonated base. Particularly preferred are catalyst salts formed from an anion of one of the aforementioned carboxylic acids and a protonated base in which the base has at least one structural unit according to the general formula I

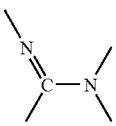

and/or according to the general Formula II

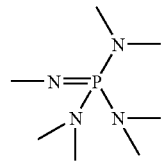

and/or according to the general Formula III.

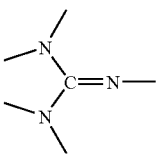

After protonation of the base, these structural units lead to good mesomeric stabilization of the positive charge, which leads to stabilization of the protonated form.

Particularly good results are obtained for the third embodiment of this invention by using as the cation a protonated base selected from the group consisting of

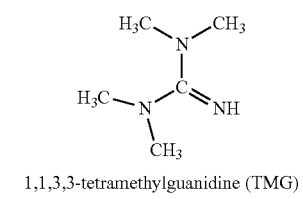
1,1,3,3-tetramethylguanidine (TMG)

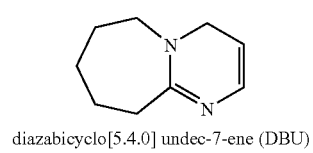
diazabicyclo[5.4.0] undec-7-ene (DBU)

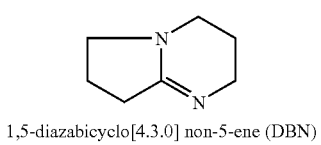
1,5-diazabicyclo[4.3.0] non-5-ene (DBN)

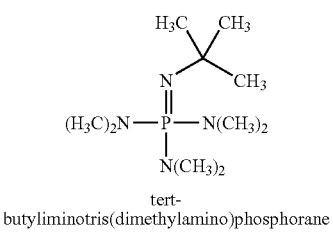
tert-butyliminotris(dimethylamino)phosphorane

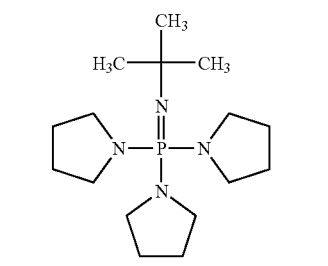
tert-butyliminotri(pyrrolidino)phosphorane

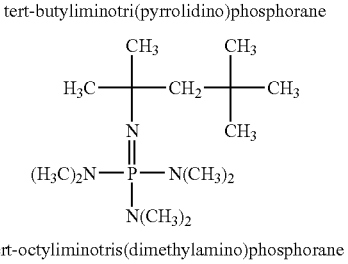
tert-octyliminotris(dimethylamino)phosphorane

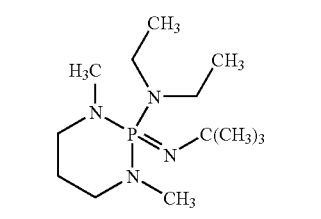
2-tert-butylimino-2-diethylamino-1,3-dimethylperhydro-1,3,2-diazaphosphorine

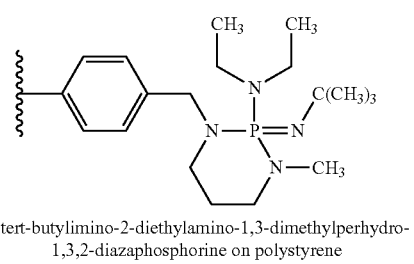
2-tert-butylimino-2-diethylamino-1,3-dimethylperhydro-1,3,2-diazaphosphorine on polystyrene

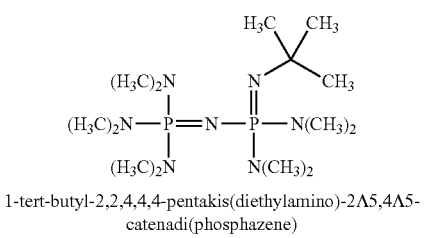
1-tert-butyl-2,2,4,4,4-pentakis(diethylamino)-2$\Lambda^5$,4$\Lambda^5$-catenadi(phosphazene)

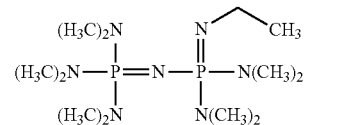
1-ethyl-2,2,4,4,4-pentakis(diethylamino)-2$\Lambda^5$, 4$\Lambda^5$-catenadi(phosphazene)

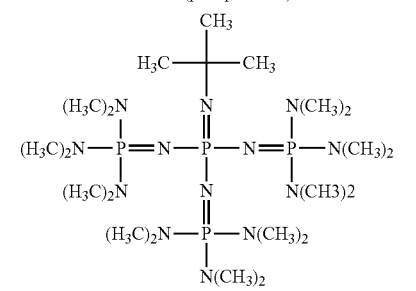
1-tert-butyl-4,4,4-tris(dimethylamino)-2,2-bis[tris(dimethylamino)phosphoranylidenamino]-2$\Lambda^5$,4$\Lambda^5$-catenadi(phosphazene)

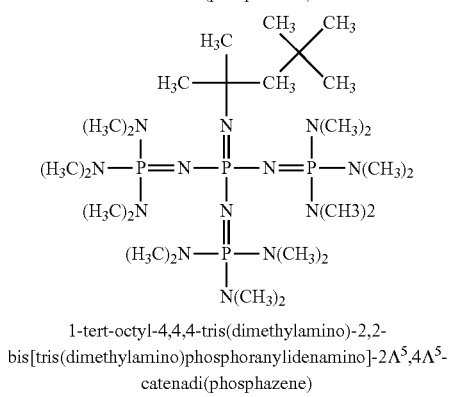
1-tert-octyl-4,4,4-tris(dimethylamino)-2,2-bis[tris(dimethylamino)phosphoranylidenamino]-2$\Lambda^5$,4$\Lambda^5$-catenadi(phosphazene)

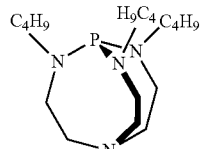
2,8,9-triisobutyl-2,5,8,9-tetraaza-1-phosphabicyclo[3.3.3]undecane

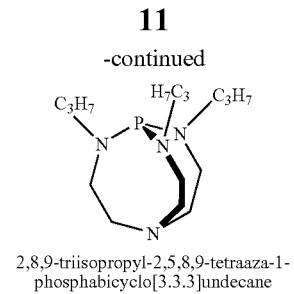

2,8,9-triisopropyl-2,5,8,9-tetraaza-1-phosphabicyclo[3.3.3]undecane

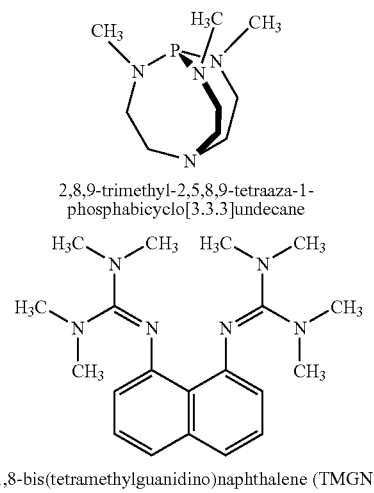

2,8,9-trimethyl-2,5,8,9-tetraaza-1-phosphabicyclo[3.3.3]undecane 1,8-bis(tetramethylguanidino)naphthalene (TMGN)

and 2-tert-butyl-1,1,3,3-tetramethylguanidine, 1,5,7-triazabicyclo(4.4.0)dec-5-ene, 7-methyl 1,5,7-triazabicyclo(4.4.0)dec-5-ene, 1,5-diazabicyclo(4.3.0)non-5-ene, and 3,3,6,9,9-pentamethyl-2,10-diazabicyclo(4.4.0)dec-1-ene.

It is preferred for the base component of the salt according to the third embodiment of this invention to be tert-butylimino-tri(pyrrolidino)phosphorane, 1-tert-butyl-2,2,4,4,4-pentakis(diethylamino)-2Λ5, 4Λ5-catenadi(phosphazene), 1-tert-butyl-4,4,4-tris(dimethylamino)-2,2-bis[tris-(dimethylamino)-phosphoranylidenamino]-2Λ$^5$,4Λ$^5$-catenadi(phosphazene), tert-octylimino-tris(dimethylamino)phosphorane, 2,8,9-tri-isopropyl-2,5,8,9-tetraaza-1-phosphabicyclo[3.3.3]undecane, 1,5-diazabicyclo[4.3.0]non-5-ene, 1,1,3,3-tetramethylguanidine, diazabicyclo[5.4.0]undec-7-ene, 7-methyl-1,5,7-triazabicyclo(4.4.0)dec-5-ene, 2-tert-butyl-1,1,3,3-tetra-methylguanidine, 1,5,7-triazabicyclo(4.4.0)dec-5-ene, and/or 1,8-bis(tetramethylguanidino)naphthalene.

The catalyst salt according to the third embodiment of this invention formed by acid-base reaction can be prepared by any method known to one skilled in the art, for example by the following reaction:

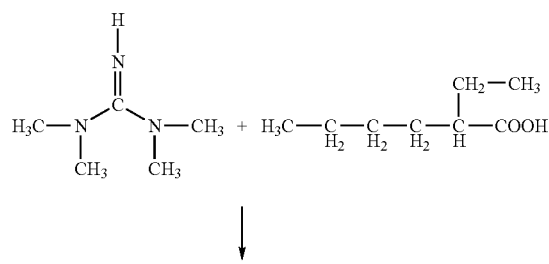

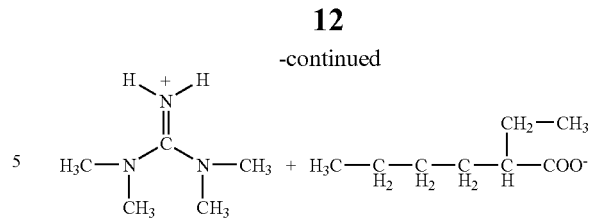

According to the invention, any salt formed from at least one of the aforementioned cations and at least one of the aforementioned carboxylate anions can be used, as a catalyst in the dental materials, with salts being preferred in particular in which the anion of the catalyst salt is an anion of a branched carboxylic acid with a length of the (cyclo)alkyl chain provided on the carboxyl group of at least 3 carbon atoms, with special preference 4, and with very special preference at least 5 carbon atoms, or of an unbranched carboxylic acid with a length of the (cyclo)alkyl chain provided on the carboxyl group of at least 5 carbon atoms. Also preferred are salts in which the anion is an anion of a saturated and/or unsaturated (cyclo)aliphatic monocarboxylic acid with a (cyclo)alkyl chain length as mentioned previously.

Especially good results are also produced in particular with salts comprising at least one aliphatic or cycloaliphatic carboxylate anion resulting from deprotonation with a (cyclo)alkyl chain that has at least one and preferably at least two branches. Preferably used as the anion of the at least one catalyst salt is an aliphatic or cycloaliphatic carboxylate anion that has at least one branch in the γ-position, with special preference at least one branch in the β-position, and with very great preference at least one branch in the α-position to the carboxyl group of the carboxylate anion. Likewise preferred are corresponding carboxylate anions in whose (cyclo)alkyl chain there is at least one branch in the γ-, β-, and/or α-position to the carboxylate anion.

In a refinement of the concept of the invention, especially for the third embodiment, in which the cation of the catalyst salt is formed by protonation of a base, it is proposed as catalyst b) in the dental material at least one salt formed from one of the aforementioned cations and an anion of an acid selected from the group consisting of 2,2-dialkylalkanoic acid, 3,3-dialkylalkanoic acid, 4,4-dialkylalkanoic acid, 2,3-dialkylalkanoic acid, 2,4-dialkylalkanoic acid, 3,4-dialkylalkanoic acid, 2,2-dialkylalkenoic acid, 3,3-dialkylalkenoic acid, 4,4-dialkylalkenoic acid, 2,3-dialkylalkenoic acid, 2,4-dialkylalkenoic acid, 3,4-dialkylalkenoic acid, 2,2-dialkylalkynoic acid, 3,3-dialkylalkynoic acid, 4,4-dialkylalkynoic acid, 2,3-dialkylalkynoic acid, 2,4-dialkylalkynoic acid, 3,4-dialkylalkynoic acid, 2-monoalkylalkanoic acid, 3-monoalkylalkanoic acid, 4-monoalkylalkanoic acid, 2,2-dialkylhexanoic acid, preferably 2,2-dialkylnonanoic acid, 2,2-dimethyldecanoic acid, 2,2-diethyldecanoic acid, 2,2-dipropyldecanoic acid, 2,2-dibutyldecanoic acid, 2,2-dimethylnonanoic acid, 2,2-diethylnonanoic acid, 2,2-dipropylnonanoic acid, 2,2-dibutylnonanoic acid, 2,2-dimethyloctanoic acid, 2,2-diethyloctanoic acid, 2,2-dipropyloctanoic acid, 2,2-dibutyloctanoic acid, 2,2-dimethylheptanoic acid, 2,2-diethylheptanoic acid, 2,2-dipropylheptanoic acid, 2,2-dibutylheptanoic acid, 2,2-dimethylhexanoic acid, 2,2-diethylhexanoic acid, 2,2-dipropylhexanoic acid, 2,2-dibutylhexanoic acid, 2-butyloctanoic acid, 2-hexyldecanoic acid, 2-propylpentanoic acid, 1-methyl-1-cyclohexanecarboxylic acid, 2,2-dimethylbutyric acid, 2,2-dimethylvaleric acid, 3,5,5,-trimethylhexanoic acid, 2-ethylhexanoic acid, decanoic acid, octanoic acid, hexanoic acid, and enanthic acid.

According to another preferred embodiment of this invention, the dental material is formulated as a two-component system and contains as catalyst b) at least one salt of diazabicyclo[5.4.0]undec-7-ene, diazabicyclo[4.3.0]non-5-ene, and/or 1,1,3,3-tetramethylguanidine with 2-alkylalkanoic acid, in particular 2-alkylhexanoic acid, 2-ethylhexanoic acid, 2,2-dialkylalkanoic acid, 2,2-dialkylhexanoic acid, 2,2-dialkylnonanoic acid, 2,2-dimethylhexanoic acid, 2,2-diethylhexanoic acid, 2,2-dimethylnonanoic acid, 2,2-diethylnonanoic acid, and/or 2-propylpentanoic acid.

In a refinement of the concept of the invention, it is proposed that the cations and/or carboxylate anions provided in the catalyst salts to be used pursuant to the invention have alkoxysilyl groups. This causes the catalyst salt to be bound into the polyether matrix after the hardening of the dental material, and to be unable any longer to be leached out of the dental impression material.

According to the invention, the dental materials can contain as catalyst b) one or more of the aforementioned salts, in any desired combination with one another. The dental material preferably contains only one of the aforementioned salts as catalyst; it is especially preferred to use no other catalysts besides the one or more salts to be used pursuant to the invention, particularly no organometallic metal salts, tertiary amines, or free acids.

In the dental material pursuant to the invention, it is preferred to use a catalyst salt b) with a pH measured in water (Ampuwa, pH 5.8) between 7 and 11, and with particular preference between 7 and 9.

One skilled in the art knows that the amount of catalyst salt to be used depends in part on the solubility of the salt in the polyether matrix used. The amount of catalyst salt to be used, based on the total dental material mixture, is preferably 0.001 to 1 mmol/g, more preferably 0.001 to 0.5 mmol/g, very preferably 0.001 to 0.1 mmol/g, and most preferably 0.005 to 0.05 mmol/g. Of course the catalyst salt used must have a minimum solubility in the polyether matrix used to be able to act catalytically at all.

To keep the amount of catalyst salt to be used as small as possible, it is proposed in a refinement of the concept of the invention to use in the dental material a catalyst salt with sufficiently high solubility in the polyether material, i.e. with adequate catalytic activity, with the catalytic activity in the context of this invention being characterized by the hardening time according to ISO 4823 (1992 version) determined by recovery after deformation. It is preferred to use a catalyst salt that produces with polytetrahydrofuran, polyethylene glycol, and with special preference polypropylene glycol, and their mixtures and copolymers as polyether matrix, a hardening time of 30 min or less, preferably 15 min or less for a dental prosthodontic composition, and a hardening time of 15 min or less, preferably 10 min or less, with special preference 7 min or less, and most preferably 6 min or less for a dental impression composition.

If the dental material pursuant to the invention is formulated as a single-component material, it should be as absolutely anhydrous as possible to avoid a reaction of the alkoxysilyl-functional polyether during storage.

If the dental material is formulated as a two-component system the catalyst component B preferably contains water, while on the other hand the base component A is as absolutely anhydrous as possible. The catalyst component B of the two-component dental material pursuant to the invention preferably contains 0.005 to 3 mmol/g, with particular preference 0.01 to 2 mmol/g, and with greatest preference 0.02 to 1 mmol/g of water.

The dental material pursuant to the invention preferably contains at least one reinforcing filler $d_1$) and/or at least one non-reinforcing filler $d_2$). For formulation as a two-component material, the base component A can contain one of the aforementioned fillers, with at least one reinforcing filler and/or at least one non-reinforcing filler preferably being provided both in the base component A and in the catalyst component B.

Suitable reinforcing fillers $d_1$) in particular are highly dispersed active fillers with a BET surface area of at least 50 $m^2$/g and/or a primary particle size of less than or equal to 100 nm, with special preference less than or equal to 80 nm. Those with a primary particle size in the nanometer range, which can be present as aggregates and/or agglomerates, are particularly suitable. The at least one reinforcing filler $d_1$) is preferably selected from the group consisting of aluminum hydroxide, zinc oxide, titanium dioxide, zirconium oxide, silicon dioxide, and precipitated and/or pyrogenic silica. Of course the aforementioned compounds can be used individually or in any combination with one another, specifically in either hydrophilic form or with water-repellent treatment.

It is also preferred for the at least one reinforcing filler $d_1$) to be in the form of nanoparticles, as fibrous or flake filler, for example mineral fibrous filler, or as synthetic fibrous filler.

In furtherance of the concept of the invention, it is proposed when formulating as two-component materials, preferably to provide reinforcing fillers $d_1$) in the base component A that have a maximum water content of 0.5 wt. %, with special preference 0.3 wt. % at the most, with very special preference 0.15 wt. %, and most preferably they are absolutely or essentially anhydrous, with the water content determined by Karl Fischer titration.

According to a further particular embodiment of this invention, the at least one reinforcing filler $d_1$) with a BET surface area of greater than 50 $m^2$/g in the base component A has a pH of 5 to 11, preferably from 5 to 9, and with special preference from 5.5 to 8.5. Degradation of the alkoxysilyl-functional polyether during storage is avoided in this way.

When formulating as a two-component system, the base component A, based on component A, preferably contains from 0 to 50 wt. %, more preferably 0.1 to 40 wt. %, and very preferably 0.1 to 30 wt. % of at least one reinforcing filler $d_1$), and the catalyst component B, based on component B, preferably contains 0 to 50 wt. %, more preferably 0.1 to 40 wt. %, and very preferably 0.1 to 30 wt. % of at least one reinforcing filler $d_1$).

Suitable non-reinforcing fillers $d_2$) in principle are the same substances as those for the reinforcing fillers $d_1$), but with the non-reinforcing fillers necessarily having a BET surface area of less than 50 $m^2$/g (Degussa Silicas, Pigment publication series, Number 12, page 5, and Number 13, page 3). The at least one non-reinforcing filler $d_2$) preferably is a substance selected from the group that consists of alkaline earth metal oxides, alkaline earth metal hydroxides, alkaline earth metal fluoride, alkaline earth metal carbonates, calcium apatite ($Ca_5[(F, Cl, OH, ½CO_3)|(PO_4)_3]$), especially calcium hydroxyapatite ($Ca_5[(OH)|(PO_4)_3]$), titanium dioxide, zirconium oxide, aluminum hydroxide, silicon dioxide, precipitated silica, and calcium carbonate. Of course the aforementioned compounds can be used individually or in any desired combination with one another, specifically either in hydrophilic form or with water-repellent treatment.

The non-reinforcing fillers $d_2$) preferably have an average particle size larger than 0.1 μm (Ullmann's Encyclopedia of Industrial Chemistry, Volume 21, page 523).

In a refinement of the concept of the invention, when formulating the dental material as a two-component system, it is proposed that the at least one non-reinforcing filler $d_2$) in the base component A have a maximum water content of 0.5 wt. %, with special preference a maximum of 0.1 wt. %, with very special preference a maximum of 0.05 wt. %, and most preferably it is absolutely or essentially anhydrous.

According to a particular embodiment of this invention, the at least one non-reinforcing filler $d_2$) in the base component A has a pH of 5 to 11, preferably from 5 to 9, and with special preference from 5.5 to 8.5, in order to avoid degradation of the alkoxysilyl-functional polyether during storage.

The base component A of the dental material pursuant to the invention, based on the component A, preferably contains 0 to 80 wt. %, with special preference 0.05 to 75 wt. %, and most preferably 0.1 to 70 wt. % of at least one non-reinforcing filler $d_2$), and the catalyst component B, based on the component B, preferably contains 0 to 80 wt. %, with special preference 0.05 to 75 wt. %, and most preferably 0.1 to 70 wt. % of at least one non-reinforcing filler $d_2$).

In a refinement of the concept of the invention, it is proposed when formulating as a two-component material, that the reinforcing and/or non-reinforcing filler contained in the catalyst component B have a pH between 6.0 and 11.0, and very especially preferred is one with a pH between 7.0 and 10.0.

The total overall content of fillers when formulating the dental materials either as a one-component system or as a two-component system, based on the total mixture, amounts to 0 to 80 wt. %, preferably 0.01 to 80 wt. %, with special preference 0.1 to 75 wt. %, and most preferably 0.2 to 70 wt. %.

In principle, all polyethers containing alkoxysilyl groups can be used as alkoxysilyl-functional polyethers a), wherein the polyether backbone can be linear and/or branched, and can be made up of polyethylene oxide, polypropylene oxide, polytetrahydrofuran, and/or their copolymers, for example, and these monomers can be arranged statistically, blockwise, or in tactic arrangement. Mono- or polyfunctional alcohols such as methanol, butanol, glycerin, trimethylolpropane, pentaerythritol, and sorbitol, for example, can be used as initiators for the polyethers and/or copolymers. For example, copolymers of polytetrahydrofuran with polyethylene oxide or of polyethylene oxide with polypropylene oxide can be used, with pure polypropylene oxide being especially preferred. Also preferred are polyethers with lateral alkyl groups, with every monomeric structural unit or at least every tenth unit carrying a lateral alkyl group. Suitable commercial products are Acclaim 4200, Acclaim 6320N, Acclaim 12200, Acclaim 8200, and Acclaim 6300 from Bayer AG, Polyglycol P41/300 and Polyglycol P41/3000 (Clariant), as well as poly (ethylene glycol-ran-polypropylene glycol) (Aldrich). The polyethers a) preferably have a number average molecular weight of 500 to 25,000 g/mol, and with special preference 5,000 to 20,000 g/mol.

In addition to chain length (elasticity), the alkoxysilyl functionalization (hardening kinetics), and the number of urethane/urea groups (viscosity, rheology), the hydrophilicity of the polyether, which is determined by the number, structure, and polarity of the monomeric repeat units of the polyether polymer, are selection criteria for the polyethers suitable for the invention. On the one hand, the hydrophilicity for a dental impression material has to be high enough to assure good flow onto wet dental substance (low contact angle), but on the other hand the material must not be too hydrophilic, since otherwise water, moisture, or saliva would lead to swelling while taking the impression or during disinfection or while filling with plaster, and the necessary dimensional accuracy would no longer exist. Furthermore, the hydrophilicity of the polyether is also co-responsible along with other factors for the polyether solubility of the catalyst pursuant to the invention.

According to a particular embodiment of this invention, the at least one alkoxysilyl-functional polyether has a content of polyether groups between 5 and 30 mmol/g, and with special preference between 10 and 25 mmol/g.

The alkoxysilyl structural unit(s) is/are terminally positioned alkoxysilyl structural units of the polyether a), based on the polymeric backbone, and fall under the general formula IV

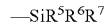

wherein $R^5$, $R^6$, and $R^7$ independently of one another are alkoxy, alkyl, aryl, aralkyl, or alkylaryl groups, or hydrogen, preferably butoxy, propoxy, ethoxy, methoxy, hexyl, pentyl, butyl, propyl, ethyl, or methyl groups, with special preference ethoxy, methoxy, ethyl, or methyl groups, provided that at least one of the aforementioned residues, preferably two or all three residues, are alkoxy groups.

In a refinement of the concept of the invention, it is proposed that the at least one polyether a) has an alkoxy group content of 0.02 to 12 mmol/g, with special preference 0.04 to 6, and most preferably 0.04 to 3 mmol/g.

The condensation kinetics and with it the processing and setting time of the dental material can be set by the nature and number of alkoxy groups per silicon atom. These parameters are preferably chosen so that the processing time is 30 seconds to 3 minutes, with special preference between 1 and 2.5 minutes, and most preferably between 1.5 and 2 minutes, and/or the maximum setting time in the patient's mouth (so-called oral residence time) is 15 minutes, with special preference 10 minutes, very preferably 7 minutes, and most preferably 6 minutes, as determined according to ISO 4823 (1992 version).

The at least one polyether a) (besides the terminal alkoxy groups and the polyether groups) preferably has a third structural unit of alkylene spacers, each located on the terminal alkoxysilyl groups, which are preferably $C_1$-$C_6$ alkyl groups, with special preference $C_1$-$C_3$ alkyl groups, very preferably ethylene groups and/or methylene groups, and most preferably methylene groups.

In addition, the at least one polyether a) as a fourth structural unit can have 0 to 8 mmol/g, with special preference 0 to 4 mmol/g, with very great preference 0.02 to 2 mmol/g, and most preferably 0.1 to 0.4 mmol/g of urethane groups and/or 0 to 8 mmol/g, with special preference 0 to 2 mmol/g, with very great preference 0.02 to 2 mmol/g, and most preferably 0.1 to 0.4 mmol/g of urea groups. Especially when the at least one polyether a) has urea and/or urethane groups as a fourth structural unit, a methylene group is preferred as spacer. Hydrophilic two-component dental impression materials stable in storage are obtained by using such α-activated alkoxysilyl polyethers, which crosslink surprisingly rapidly by a condensation reaction with a salt to be used as catalyst according to the invention. The overall content of urethane or urea groups per molecule should be kept as small as possible in order to minimize intermolecular interactions between the individual polyether chains, to keep the viscosity caused by the polyether additive as low as possible, which allows the addition of larger amounts of fillers in the dental materials and thus allows more freedom in formulation and more economical formulations.

It has proved to be advantageous in the context of this invention to use polyethers that contain no urethane or urea groups within the polymer chain and that carry no more than one urethane or urea group at the most, and no more than one (alkoxy)silyl group at the most, and no more than one methylene spacer group at the most, at each end of the chain. The use of these polyethers leads to formulations with lower viscosity than the polyurethane-alkoxysilyl polyethers used in the state of the art, so that more fillers can be added to the dental materials, which leads to a reduction of production costs.

According to another particular embodiment of this invention, the individual structural units of the at least one polyether a) are arranged as follows:

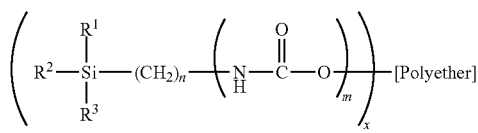

wherein $R^1$, $R^2$, and $R^3$ independently of one another are alkoxy, alkyl, aryl, aralkyl, alkylaryl groups, or hydrogen, preferably butoxy, propoxy, ethoxy, methoxy, hexyl, pentyl, butyl, propyl, ethyl, or methyl groups, with special preference ethoxy, methoxy, ethyl, or methyl groups, provided that at least one of the aforementioned residues, preferably two or all three residues, are alkoxy groups, and x=1 to 6, preferably x=2 to 4, and with special preference x=2, n=1 to 6, preferably n=1 to 3, and with special preference n=1, and m=0 or 1, with special preference m=1, or

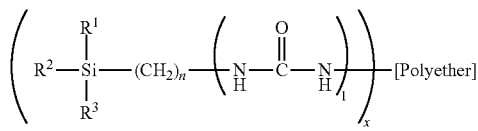

wherein $R^1$, $R^2$, and $R^3$ independently of one another are alkoxy, alkyl, aryl, aralkyl, alkylaryl groups, or hydrogen, preferably butoxy, propoxy, ethoxy, methoxy, hexyl, pentyl, butyl, propyl, ethyl, or methyl groups, with special preference ethoxy, methoxy, ethyl, or methyl groups, provided that at least one of the aforementioned residues, preferably two or all three residues, are alkoxy groups, and x=1 to 6, preferably x=2 to 4, and with special preference x=2, n=1 to 6, preferably n=1 to 3, and with special preference n=1, and l=0 or 1, and with special preference l=1.

According to a particular embodiment of this invention, the alkyl spacer in the aforementioned structural units is methylene (n=1).

The preparation of these alkoxysilyl-functional polyethers is known and is described, for example in DE 101 04 079 A1, EP 0 629 819 B1, DE 101 39 132, U.S. Pat. No. 4,906,707, EP 0 372 561 A1, EP 1 303 560 A1, and EP 0 170 865 B1, which are hereby introduced as references and are part of the disclosure. Examples of commercially obtainable polyethers suitable in the context of this invention are MS Polymer S 203H, MS Polymer S 303H (Kaneka), Polymer XP ST55, ST50, ST51, ST53 (Hanse), SLM 414000 (Wacker), SLM 414001 (Wacker), Baycoll XP 2458, and Desmoseal XP 2447 (Bayer AG), with dimethoxy(methyl)silylmethylcarbamate-terminated polyether sold under the trade name SLM 414000:

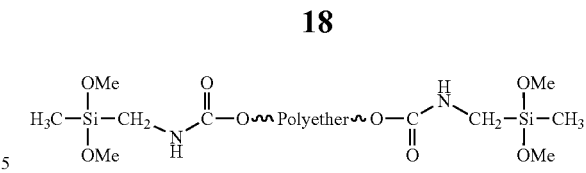

and dimethoxy(methyl)silylmethylurea-terminated polyether:

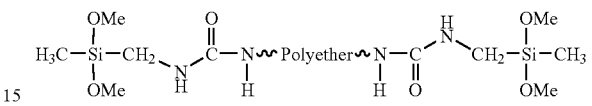

being particularly preferred.

In furtherance of the concept of the invention, it is proposed that one or more of the following additives and/or auxiliaries be added to the dental material pursuant to the invention:
f) Thixotropic agent,
g) Water scavenger,
h) Paste-former,
i) Surfactant,
j) Active ingredient,
k) Plasticizer,
l) Optical scanning facilitator,
m) Flavor and/or odorant,
n) Diagnosis facilitator,
o) Fluoridation agent,
p) Bleach,
q) Desensitizing agent,
r) Bonding agent,
s) Colorant,
t) Indicator,
u) Stabilizer (antioxidant, free radical scavenger)

Thixotropic agents f) can optionally be added to the dental material pursuant to the invention, for which high molecular weight polyethers such as polyethylene glycol, polyethylene glycol/polypropylene glycol copolymers, polytetrahydrofuran, hydrocarbon waxes, amide waxes, triglycerides, silicas, and silicates have proved to be particularly suitable.

According to a further particular embodiment of this invention, the dental materials, when formulated as a two-component system, in the base component A preferably have at least one water scavenger g), which is selected with special preference from the group that consists of alkoxysilanes, titanates such as tetraisopropyl titanate, zirconates such as tetrapropyl zirconate, zeolites, aluminum sulfate, anhydrous calcium sulfate (e.g. Drierite®), Blue Gel, and/or oxazolidines.

In a refinement of the concept of the invention, it is proposed to use as water scavenger g) one or more functional alkoxysilanes, since the speed of crosslinking, the structure, and the properties of the resultant elastomer can be adjusted additionally by such compounds. It is preferred for the at least one functional alkoxysilane to be a compound with the general formula V $R^8{}_{4-x}$—Si—$R^9{}_x$ wherein $R^8$=H, alkyl, alkenyl, —$(CH_2)_n$—Z, with n=1 to 6,
$R^9$=Alkoxy,
Z=$NH_2$, NHR, $NR_2$, with R=Alkyl, aminoalkyl, —C(O)$OCH_3$, and
x=1, 2, 3, or 4,
wherein it is especially preferred if $R^8$=alkenyl, especially vinyl, or —$(CH_2)_n$—Z, with Z=NHR and n=1 or 3, especially n=1, and/or x=3 and/or R=—C(O)OCH$_3$.

It is particularly preferred for the at least one functional alkoxysilane g) to be vinyltrimethoxysilane, N-trimethoxysilylmethyl-O-methylcarbamate and/or a compound with the following formula:

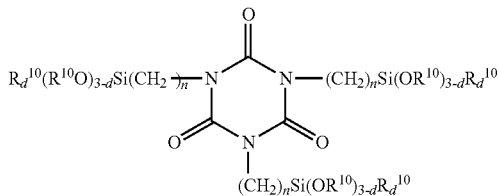

wherein n=1 to 6, preferably n=1 or 3, with special preference n=1, d=0 or 1, and $R^{10}$=a linear or branched $C_1$-$C_{30}$ alkyl group in which the hydrogen atoms may be partially substituted by halogen atoms, OH—, NH$_2$—, NO$_2$—, or other $C_1$-$C_6$ alkyl groups.

The aforementioned compounds are reactive silanes that function as water scavengers to eliminate traces of water still present in component A of the dental composition.

Specifically when it is formulated as a two-component system, the two-component dental material pursuant to the invention preferably also contains in the catalyst component B at least one paste-former h), since this permits setting a paste-like consistency, for example free-flowing, semifluid, or high-viscosity, and makes possible a homogeneous blending of the salt and the solid reinforcing and non-reinforcing fillers. Preferably used as at least one paste-former h) is a compound selected from the group that consists of polyethers, polyvinylpyrrolidones, polyurethanes, polyesters, waxes, vaseline, paraffin oils, silicone oils, polyfunctional alcohols, propylene glycol, polypropylene glycols, ethylene glycols, polyethylene glycols, copolymers of N-vinylpyrrolidone and vinyl acetate, carboxymethyl-, methyl-, hydroxyethyl-, hydroxypropylcellulose, polysaccharides, glycerin, and poly(meth)acrylic acids. Of course the dental materials pursuant to the invention may also contain any combination of two or more of the aforementioned compounds.

Hydrophilic paste-formers in which the catalyst base can be mixed homogeneously with water are especially preferred. The miscibility can be improved further by adding surfactants. Particularly preferred representatives are polyethers, polyurethanes, polyesters, polyfunctional alcohols, especially propylene glycols, polypropylene glycols, ethylene glycols, polyethylene glycols, butylene glycols, polybutylene glycols, and glycerin, as well as their mixtures and copolymers.

The compounds i) optionally used as surfactant, emulsifier, and/or stabilizer are preferably anionic surfactants, with special preference alkyl sulfates, alkylbenzenesulfonates, or alkylbenzenephosphates, cationic surfactants, with special preference tetraalkylammonium halides, nonionic surfactants, with special preference alkyl- and alkylphenyl polyalkylalkylene oxides, fatty acid alkoxylates, fatty alcohol alkoxylates and their alkyl ethers and alkyl esters, fatty acid alkylolamides, sucrose fatty acid esters, trialkylamine oxides, silicone surfactants (e.g. Silwet L77, Tegopren 5878), or fluoro surfactants, or amphoteric surfactants, with special preference sulfated or ethoxylated condensation products of alkenylphenols and formaldehyde, ethylene oxide/propylene oxide block polymers, or modified polysiloxanes. Surfactants that can be copolymerized into the alkoxysilyl-functional polyethers a), such as those disclosed in U.S. Pat. No. 4,160,778, can also be used advantageously and are hereby introduced as a reference and disclosed as part of the disclosure. In addition or alternatively thereto, derivatives of the aforementioned surfactants can also be used, for example those that have functional groups such as —OH, —CH=CH$_2$, —OCO—(CH$_3$)C=CH$_2$, and alkoxysilyl groups. Also, other surfactants known to one skilled in the art can be used, although less preferably.

It is preferred to use a silicone surfactant as the used compound i), since it has been found surprisingly in the course of this invention that very low contact angles can be produced in the polyether matrix with these compounds, as determined by the "sessile drop" method.

These mixtures are distinguished by excellent wettability and outstanding flow properties onto wet dental and tissue substance.

Despite these good hydrophilic properties, the material does not swell in contact with aqueous media such as water, saliva, blood, disinfectant bath, or aqueous plaster slurry. The good initial wettability of the mixtures is important for the accurately detailed impression from the impression material in the patient's mouth during processing and in the first contact with wet oral/dental substance, and is manifested by a low contact angle of less than 50°, in particular less than or equal to 45°, measured with a contact angle measuring instrument from the Kruss Company at 20° C. by the "sessile drop" method. In addition, the hardened impression at the time of filling with plaster (immediately or 2 hours after hardening) is distinguished by a contact angle smaller than 60°, in particular less than or equal to 55°.

Also, the dental materials pursuant to the invention may contain one or more active ingredients j), that may be present in the base component A or the catalyst component B, depending on their chemical functionality when formulated as a two-component system. Among the active ingredients to be used pursuant to the invention in particular are astringents such as epinephrine, substances with antibacterial and/or antifungal activity such as hexitidine (e.g. 5-amino-1,3-bis(2-ethylhexyl)-5-methylhexahydropyrimidine), triclosan (e.g. 2,4,4'-trichloro-2-hydroxydiphenyl ether), and chlorhexidine:

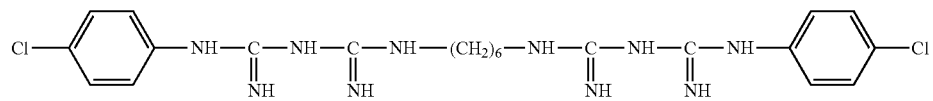

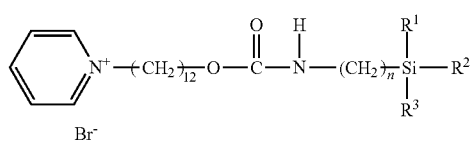

wherein $R^1$, $R^2$, and $R^3$ independently of one another are alkoxy, alkyl, aryl, aralkyl, alkylaryl groups, or hydrogen, preferably butoxy, propoxy, ethoxy, methoxy, hexyl, pentyl, butyl, propyl, ethyl, or methyl groups, with particular preference ethoxy, methoxy, ethyl, or methyl groups, provided that at least one of the aforementioned groups, preferably two or all three groups, are alkoxy groups.

Useful plasticizers k) in particular are unreactive polyethers, polyesters, polyurethanes, phthalates, mono-, di-, tri-, or higher-functional esters, particularly acetyl(tributyl citrate), Mesamoll® (Bayer), and triglycerides, which are added to component A and/or to component B depending on their chemical nature, when formulating as a two-component system.

As compounds l) that enable optical reading/scanning, all substances known to one skilled in the art for this purpose, particularly metal powders, metal pigments, metallic pigments, zinc oxide, zirconium oxide, and titanium dioxide, can be added to component A and/or to component B, depending on their chemical nature, when formulating as a two-component system.

In addition, the dental materials pursuant to the invention can contain in one of the two components, or in both of them, the usual flavors and/or odorants m) and/or the additives n) useful for diagnostics, as described, for example, in EP 1 339 373, PCT/EP00/05418, and DE 100 61 195.

Fluoridation agents that have proved particularly suitable are sodium fluoride, potassium fluoride, ammonium fluoride, fluorophosphates, and amine fluorides such as N'-octadecyl-bimethylenediamine-N,N,N'-bis(2-ethanol)dihydrofluoride (as described in ZM 93, Number 15, pages 32 ff.); they can be added to component A and/or to component B when formulating as a two-component system, likewise depending on their chemical nature.

The dental material pursuant to the invention when formulated as a two-component system can also contain one or more different peroxides in component A and/or component B as bleaches p), which are preferably selected from the group that consists of alkali metal and alkaline earth metal peroxides, hydrogen peroxide, and carbamide peroxide.

Examples of suitable desensitizing agents q) are potassium salts such as potassium nitrate, oil of cloves, and eugenol.

Alkoxysilanes, epoxysilanes, aminosilanes, and methacrylate silanes are especially suitable as bonding agents r), for example to develop an adhesive bond between the impression material and a stainless steel or plastic impression mold.

Examples of suitable colorants s) are dyestuff pigments in the form of Al, Ca, Ba oxides/laked colorant, which like the previously described auxiliary substances, if not otherwise indicated, can be added to component A and/or to component B when formulating as a two-component system, depending on their chemical nature.

When formulating as a two-component system, dye indicators t) can also be added to the dental material pursuant to the invention in component A and/or in component B that change color as a function of pH, for example because of pH changes when mixing components A and B, or upon contact with water.

Compounds can be added to the two-component dental materials pursuant to the invention as stabilizers and/or antioxidants u), in particular those selected from the group consisting of polymeric trimethyldihydroquinoline, diphenyl derivatives, phenothiazine, phenyl-α-naphthylamine, 4,4'-methylenebis(2,6-di-tert-butylphenol), butylhydroxytoluene, butylhydroxyanisole (BHA), and methoxyphenol (hydroxyanisole). Examples of such compounds are the products commercially available from the Ciba-Geigy Company Irganox 1010, 1076, 1035, MD 1024, Irgafos 168, 38, Irgacor 252 LD/252FC, 1405, 1930, 153, Tinuvin 328, P, 384, 900, 928, 327, 1130, 400, 292, 144, 123, 622, and Chimassorb 119.

The two-component dental material pursuant to the invention is preferably packed and proportioned properly for later use in suitable primary packages such as tubes, cans, and with special preference in cartridges and foil bags such as those described in EP 0 723 807 A2, EP-A-0 541 972, PCT/EP/980193, EP-A-0 492 412, EP-A-0 492 413, and EP 0 956 908 A1, which are hereby introduced as references and thus are part of the disclosure.

Another object of this invention is mixtures that are obtainable by blending components A and B of the previously described two-component dental material pursuant to the invention. The base component A is preferably blended with the catalyst component B in a ratio of 1:1 to 20:1, with special preference from 1:1 to 10:1, and most preferably a ratio of 1:1, 2:1, 4:1, or 5:1.

The invention will be explained below with reference to examples that demonstrate the concept of the invention but do not limit it.

EXAMPLES 1 TO 12

Pursuant to the Invention (Preparation of Various Catalyst Components B with Catalyst Salts Formed from 2-ethylhexanoic Acid and Various Strong bases in Accordance with the Third Form of Embodiment of this Invention)

Preparation of Various Catalyst Components B

Various catalyst salts formed from the amounts of strong bases and 2-ethylhexanoic acid listed in Table 1 were dissolved in 5.0 parts of demineralized water (Ampuwa, pH 5.8). The individual salt solutions were then mixed for 5 minutes in a vacuum mixer cup with 36 parts of polypropylene glycol with a molecular weight of 4,000 g/mol, 51 parts of aluminum hydroxide with an average particle size of 13 μm and a BET surface area of less than 1 $m^2/g$, and 5 parts of silica with a BET surface area of 130 $m^2/g$. Mixing was then continued for 30 minutes longer under vacuum until the mixture was homogeneous.

Medium viscosity materials (ISO 4823) were obtained that represent various catalyst components B of the impression material pursuant to the invention based on alkoxysilylpolyethers. The materials were loaded into tube bags (PE/Al/PE composite films) and stored.

Preparation of a Base Component A

In a vacuum mixer, 39 parts of a polypropylene glycol that was functionalized terminally with dimethoxymethylsilyl groups through urethane groups and methylene spacers, with the functionalized polypropylene glycol having a viscosity at 20° C. of 10,000 mPa·s, was mixed for 5 minutes with 51 parts of a dried cristobalite filler surface-modified with trimethylsilyl groups, with an average particle size of 7 μm, 7 parts of a dried, microdispersed, pyrogenically produced silicic acid rendered hydrophobic, with a BET surface area of 170 $m^2/g$, 0.4 parts of vinyltrimethoxysilane, 0.4 parts of N-trimethoxysilylmethyl-O-methylcarbamate, and 2 parts of a silicone surfactant. Mixing was then continued for 30 minutes longer under vacuum until the mixture was homogeneous.

Medium viscosity materials (ISO 4823) were obtained that represent the base component A of the impression material pursuant to the invention based on alkoxysilylpolyethers. The materials were loaded into foil bags (PE/Al/PE composite film), and stored.

Mixture of Catalyst Components B and the Base Component A

One part of each of the previously described catalyst components B and 5 parts of the base component A prepared according to the instructions above were mixed homogeneously using an electric dispenser for foil bags (Plug & Press System, Kettenbach GmbH & Co. KG) through a dynamic mixer (Kettenbach GmbH & Co. KG).

The setting times of the dental materials based on alkoxysilylpolyethers prepared in this way are shown in Table 1, and other application-related properties are shown in Tables 3, 4, and 5 for the dental material obtained in Example 9.

Examples 1 to 12 show that the compositions pursuant to the invention, containing as catalyst a salt formed from a strong base with a $pK_{BH+}$ greater than 20 measured in acetonitrile and 2-ethylhexanoic acid, surprisingly have outstanding hardening kinetics for condensation-crosslinking alkoxysilylpolyether systems. Fast-setting impression materials with processing times proper for practical use can be prepared. One skilled in the art recognizes that the setting times of the individual examples can readily be adjusted as desired by increasing or reducing the amount of catalyst salt used.

As Table 5 shows in particular for the compositions in Example 9, the dental materials pursuant to the invention meet all the requirements for a functional dental impression material, especially with regard to Shore A hardnesses, recovery after deformation, consistencies of the individual components and of the mixture, linear dimensional changes, and contact angles. In particular, outstanding values are obtained for the hydrophilicity determined by measuring the contact angle.

COMPARISON EXAMPLES 1 TO 7

Not Pursuant to the Invention

Various salts from the amounts of weak bases indicated in Table 1 and 2-ethylhexanoic acid were dissolved in 5.0 parts of demineralized water (Ampuwa, pH 5.8) and were processed into a catalyst component B in the same way as in Examples 1 to 12.

One part of each of the previously described catalyst components B and 5 parts of the base component A according to Example 1 were mixed homogeneously using an electric dispenser for foil bags (Plug & Press System, Kettenbach GmbH & Co. KG) through a dynamic mixer (Kettenbach GmbH & Co. KG).

The setting times of the materials based on alkoxysilylpolyethers prepared in this way are shown in Table 1.

As is apparent from Table 1, the materials prepared in Comparison Examples 1 to 7, in each of which a salt formed from 2-ethylhexanoic acid and a base with a $pK_{BH+}$ below 20 was used as catalyst, in contrast to the formulations according to the invention, have unacceptable setting times of more than 60 minutes, or do not react.

EXAMPLES 13 TO 40

Pursuant to the Invention (Preparation of Various Catalyst Components B with Catalyst Salts Formed Pursuant to the Invention from Various Strong Bases and Various Acids)
Preparation of Various Catalyst Components B Various catalyst salts formed from the amounts of strong base indicated in Table 2 and saturated and unsaturated (cyclo)aliphatic carboxylic acids were dissolved in 5.0 parts of demineralized water (Ampuwa, pH 5.8). The individual salt solutions were then mixed for 5 minutes in a vacuum mixer cup with 36 parts of polypropylene glycol with a molecular weight of 4,000 g/mol, 51 parts of aluminum hydroxide with an average particle size of 13 μm and a BET surface area of less than 1 m²/g, and 5 parts of silica with a BET surface area of 130 m²/g. Mixing was then continued for 30 minutes longer under vacuum until the mixture was homogeneous.

Medium viscosity materials (ISO 4823) were obtained that represent various catalyst components B of the impression material pursuant to the invention based on alkoxysilylpolyethers. The materials were loaded into tube bags (PE/Al/PE composite films) and stored.

Mixture of the Catalyst Components B and the Base Component A from Example 1

One part of each of the previously described catalyst components B and 5 parts of the base component A prepared according to Example 1 were mixed homogeneously using an electric dispenser for foil bags (Plug & Press System, Kettenbach GmbH & Co. KG) through a dynamic mixer (Kettenbach GmbH & Co. KG).

The setting times of the dental materials prepared in this way based on alkoxysilylpolyethers are shown in Table 2.

Examples 13 to 40 show that the compositions pursuant to the invention, containing as catalyst a salt composed of a cation of bases with a $pK_{BH+}$ greater than 20 measured in acetonitrile and an anion formed by deprotonation of a saturated carboxylic acid with the length of the alkyl chain provided on the carboxyl group being at least 2 carbon atoms, or of an unbranched carboxylic acid with the length of the alkyl chain provided on the carboxyl group being at least 4 carbon atoms, preferably a branched carboxylic acid with the length of the (cyclo)alkyl chain provided on the carboxyl group being at least 3 carbon atoms, or an unbranched carboxylic acid with the length of the (cyclo)alkyl chain provided on the carboxyl group being at least 5 carbon atoms, surprisingly have outstanding hardening kinetics for condensation-crosslinking systems. Fast-setting impression materials with processing times proper for practical use can be prepared. One skilled in the art recognizes that the setting times of the individual examples can readily be adjusted as desired by increasing or reducing the amount of catalyst salt used.

COMPARISON EXAMPLES 8 TO 19

Not Pursuant to the Invention

Various catalyst salts formed from the amounts of strong bases listed in Table 2 and various carboxylate anions were dissolved in 5.0 parts of deionized water (Ampuwa, pH 5.8) and were then processed into a catalyst component B in the same way is in Examples 13 to 40.

One part of each of the previously described catalyst components B and 5 parts of the base component A according to Example 1 were mixed homogeneously using an electric dispenser for foil bags (Plug & Press System, Kettenbach GmbH & Co. KG) through a dynamic mixer (Kettenbach GmbH & Co. KG).

The setting times of the materials based on alkoxysilylpolyethers prepared in this way are shown in Table 2.

It can be seen from Table 2 that the materials prepared in Comparison Examples 8 to 19, in each of which a salt of an acid anion not pursuant to the invention was used as catalyst, in contrast to the formulations pursuant to the invention, have unacceptable setting times of more than 30 minutes, or do not react.

COMPARISON EXAMPLE 20

Not Pursuant to the Invention (Acid-Catalyzed Condensation-Crosslinking Dental Material Based on Alkoxysilylpolyethers According to Examples 3 and 5 of EP 1 226 808 A2)

An acid-catalyzed dental material according to the state of the art based on alkoxysilylpolyethers consisting of an acidic catalyst component B and a base component A is prepared and mixed in accordance with Examples 3 and 5 of EP 1 226 808 A2.

The processing time, setting time, and setting time after a thermal stress test of one week at 60° C. of the composition prepared according to Comparison Example 20 are shown in Table 3 compared with the dental material based on alkoxysilylpolyethers pursuant to the invention obtained in Example 9.

Compared to the dental materials pursuant to the invention based on alkoxysilylpolyethers, the acid-catalyzed system from EP 1 226 808 A2 (Examples 3 and 5) no longer shows hardening after storage in the thermal stress test (one week 60° C.). This shows that the catalyst component from Example 3 of EP 1 226 808 A2 is unstable. This leads to a lengthened setting time. A setting time that stays the same regardless of storage time is, of course, one of the most important requirements for a dental impression material.

EXAMPLE 9a TO 9e

Pursuant to the Invention

Various astringent and/or antibacterial additives were added to the catalyst component B prepared in Example 9, in the amounts shown in Table 4, and were loaded into tube bags (PE/Al/PE composite films) and stored. One part of each of these catalyst components B and 5 parts of the base component A prepared according to Example 9 were mixed homogeneously using an electric dispenser for foil bags (Plug & Press System, Kettenbach GmbH & Co. KG) through a dynamic mixer (Kettenbach GmbH & Co. KG).

The setting times and setting time after a thermal stress test of one week at 60° C. of the dental materials prepared in this way are shown in Table 4, and other application-related properties for the dental material obtained in Example 9c are shown in Table 5.

As shown by Table 4, the addition of astringent and/or antibacterial additives has no effect, or only a negligibly small effect, on the setting time and the storage stability of the compositions pursuant to the invention. As can also be seen from Table 5, the dental materials pursuant to the invention meet all of the requirements for dental materials despite the addition of astringent and/or antibacterial agents.

EXAMPLE 41

Preparation of a Catalyst Component B with a Catalyst Salt Formed from a Crown Ether-Alkali Metal Complex Cation and the 2-ethylhexanoate Anion in Accordance with the First Form of Embodiment of this Invention 1.37 parts of 2-ethylhexanoic acid was dissolved in 5 parts of demineralized water (Ampuwa, pH 5.8) and neutralized with 0.53 part of potassium hydroxide, 2.51 parts of a crown ether of the 18-crown-6 type was added, and the mixture was subjected to intensive stirring until the crown ether had completely dissolved. The salt solution was mixed for 5 minutes in a vacuum mixer with 36 parts of polypropylene glycol with a molecular weight of 4,000 g/mol, 51 parts of aluminum hydroxide with an average particle size of 13 µm and a BET surface area of less than 1 m$^2$/g, and 5 parts of silica with a BET surface area of 130 m$^2$/g. Mixing was then continued for 30 minutes longer under vacuum until the mixture was homogeneous.

A medium viscosity material (ISO 4823) was obtained that represents the catalyst component B of the dental material pursuant to the invention based on alkoxysilylpolyethers. The material was loaded into a tube bag (PE/Alu/PE composite film) and stored.

Mixture of Catalyst Component B from Example 41 and the Base Component A from Example 1

One part of the previously described catalyst component B and 5 parts of the base component A according to Example 1 were mixed homogeneously using an electric dispenser for foil bags (Plug & Press System, Kettenbach GmbH & Co. KG) through a dynamic mixer (Kettenbach GmbH & Co. KG).

The setting times of the dental materials based on alkoxysilylpolyethers with a catalyst salt of crown ether-potassium complex cation with 2-ethylhexanoate anion surprisingly has outstanding setting hardening kinetics for condensation-crosslinking alkoxysilylpolyether systems. Fast-setting impression materials with processing times proper for practical use can be prepared.

The pH of the aforementioned catalyst salt is about pH 7, in the neutral region, so that in this case there is exceptionally good mucosal tolerance in the patient's mouth.

TABLE 1

Composition and binding time of the compositions according to Examples 1 to 12 and Comparison Examples 1 to 7

| Example pursuant to the invention/ Comparison Example | Strong base | Weak acid | Base (%) [mmol/g] | Acid (%) [mmol/g] | p$K_{BH+}$ Base (H$_2$O) | p$K_{BH+}$ Base (MeCN) | Setting time |
|---|---|---|---|---|---|---|---|
| Example 1 | tert-Butyliminotri(pyrrolidino)phosphorane | 2-Ethylhexanoic acid | 2.97 [3.20] | 1.37 [6.93] | | 28.4[2)] | <1 min. |
| Example 2 | 1-tert-Butyl-2,2,4,4,4-pentakis(dimethylamino)-2$\Lambda^5$,4$\Lambda^5$-catenadi(phosphazene) | 2-Ethylhexanoic acid | 3.49 [2.72] | 1.37 [6.93] | | 33.5[2)] | <1 min. |
| Example 3 | 1-Ethyl-2,2,4,4,4-pentakis(dimethylamino)-2$\Lambda^5$,4$\Lambda^5$-catenadi(phosphazene) | 2-Ethylhexanoic acid | 3.22 [2.95] | 1.37 [6.93] | | 32.9[2)] | <1 min. |

TABLE 1-continued

Composition and binding time of the compositions according to Examples 1 to 12 and Comparison Examples 1 to 7

| Example pursuant to the invention/ Comparison Example | Strong base | Weak acid | Base (%) [mmol/g] | Acid (%) [mmol/g] | $pK_{BH+}$ Base ($H_2O$) | $pK_{BH+}$ Base (MeCN) | Setting time |
|---|---|---|---|---|---|---|---|
| Example 4 | 1-tert-Butyl-4,4,4-tris(dimethylamino)-2,2-bis([tris(dimethylamino)phosphoranyiden-amino]-2Λ5,4Λ5-catenadi(phosphazene) | 2-Ethylhexanoic acid | 6.02 [1.58] | 1.37 [6.93] | | 41.9[2] | <1 min. |
| Example 5 | tert-Octyliminotris(dimethylamino)phosphorane | 2-Ethylhexanoic acid | 2.76 [3.44] | 1.37 [6.93] | | 26.5[2] | 5'00" |
| Example 6 | 2,8,9-Triisopropyl-2,5,8,9-tetraaza-1-phosphabicyclo[3.3.3]undecane | 2-Ethylhexanoic acid | 2.42 [3.92] | 1.37 [6.93] | | 33.63[3] | 5'30" |
| Example 7 | 1,5-Diazabicyclo[4.3.0]non-5-ene | 2-Ethylhexanoic acid | 1.18 [8.05] | 1.37 [6.93] | | 23.89[2] | 6'00" |
| Example 8 | 1,1,3,3-Tetramethylguanidine | 2-Ethylhexanoic acid | 1.09 [8.68] | 1.37 [6.93] | | 23.3[2] | 6'00" |
| Example 9 | 1,8-Diazabicyclo[5.4.0]undec-7-ene | 2-Ethylhexanoic acid | 1.45 [6.57] | 1.37 [6.93] | 12[4] | 24.33[2] | 7'00" |
| Example 10 | 7-Methyl-1,5,7-triazabicyclo[4.4.0]dec-5-ene | 2-Ethylhexanoic acid | 1.46 [6.53] | 1.37 [6.93] | | 25.44[2] | 7'30" |
| Example 11 | 2-tert-Butyl-1,1,3,3-tetramethylguanidine | 2-Ethylhexanoic acid | 1.63 [5.84] | 1.37 [6.93] | 14[7] | >20 | 9'30" |
| Example 12 | 1,5,7-Triazabicyclo[4.4.0]dec-5-ene | 2-Ethylhexanoic acid | 1.32 [7.18] | 1.37 [6.93] | | 25.98[2] | 10'00" |
| Comparison Example 1 | 2-Methylimidazole | 2-Ethylhexanoic acid | 0.78 [12.18] | 1.37 [6.93] | 7.80[10] | <20 | >60 min. |
| Comparison Example 2 | 4-Methylimidazole | 2-Ethylhexanoic acid | 0.78 [12.18] | 1.37 [6.93] | 7.45[10] | <20 | >60 min. |
| Comparison Example 3 | N-Methylimidazole | 2-Ethylhexanoic acid | 0.78 [12.18] | 1.37 [6.93] | 6.95[5] | <20 | >60 min. |
| Comparison Example 4 | Triethanolamine | 2-Ethylhexanoic acid | 0.42 [6.70] | 1.37 [6.93] | 7.77[9] | <20 | No Reaction |
| Comparison Example 5 | 1,2,2,6,6-Pentamethylpiperidine | 2-Ethylhexanoic acid | 1.48 [6.44] | 1.37 [6.93] | 11.25[6] | 18.62[2] | No reaction |
| Comparison Example 6 | Tributylamine | 2-Ethylhexanoic acid | 1.76 [5.39] | 1.37 [6.93] | | 18.09[2] | No reaction Phase separation Insoluble |
| Comparison Example 7 | Triphenylphosphine | 2-Ethylhexanoic acid | 2.49 [3.81] | 1.37 [6.93] | 2.73[8] | <20 | No reaction Phase separation Insoluble |

[2] Source: ChemFiles: Strong and Hindered Bases in Organic Synthesis, Vol. 3, No. 1, Fluka
[3] Topics in Current Chemistry, Vol. 223, John G. Verhade "P(RNCH$_2$CH$_2$)$_3$N: Very Strong Non-Ionic Bases Useful in Organic Synthesis"
[4] http://www.cem.msu.edu/~reusch/VirtualText/suppmnt2.htm
[5] Source: http://www.zirchrom.com/organic.htm, "Dissociation constants of organic acids and bases"
[6] Source: H. Z. Sommer, H. I. Lipp, L. L. Jackson, J. Org. Chem., Vol. 36, No. 6 (1971) 824
[7] 50% in ethanol, Source: DHR Baron, J. D. Elliott, SD Gero, J. Chem. Soc. Perkin Trans. I 1982, 2085
[8] 50% in ethanol, Source: W. A. Henderson, C. A. Strueli, J. Am. Chem. Soc. 1960, 82, 5791
[9] Source: H. K. Hall, J. Am. Chem. Soc. 1957, 79, 5441
[10] Source: M. Schmidt am Busch, E. W. Knapp ChemPhysChem 2004, 5, 1513-1522

TABLE 2

Composition and binding time of the compositions according to Examples 13 to 40 and Comparison Examples 8 to 19

| Example pursuant to the invention/ Comparison Example | Strong base | Weak acid | Base (%) [mmol/g] | Acid (%) [mmol/g] | $pK_{BH+}$ Base (MeCN) | Number of C atoms of longest C chain | Number of Substituents in the longest C chain of the acid[2] | Setting time |
|---|---|---|---|---|---|---|---|---|
| Example 13 | 1,1,3,3-Tetramethylguanidine | 2,2-Dimethylnonanoic acid | 1.09 [8.68] | 1.77 [5.35] | 23.3[3] | 8 | (α, α')**2 | 4'00" |
| Example 14 | 1,5-Diazabicyclo[4.3.0]non-5-ene | 2,2-Dimethylhexanoic acid | 1.18 [8.05] | 1.37 [6.93] | 23.89[3] | 5 | (α, α')**2 | 4'45" |

TABLE 2-continued

Composition and binding time of the compositions according to Examples 13 to 40 and Comparison Examples 8 to 19

| Example pursuant to the invention/ Comparison Example | Strong base | Weak acid | Base (%) [mmol/g] | Acid (%) [mmol/g] | pK$_{BH+}$ Base (MeCN) | Number of C atoms of longest C chain | Number of Substituents in the longest C chain of the acid[2] | Setting time |
|---|---|---|---|---|---|---|---|---|
| Example 15 | 1,1,3,3,-Tetramethylguanidine | 2,2-Dimethylhexanoic acid | 1.09 [8.68] | 1.37 [6.93] | 23.3[3] | 5 | (α, α')**2 | 5'00" |
| Example 16 | 1,8-Diazabicyclo[5.4.0]undec-7-ene | 2,2-Dimethylnonanoic acid | 1.45 [6.57] | 1.77 [5.37] | 24.33[3] | 8 | (α, α')**2 | 5'00" |
| Example 17 | 1,5-Diazabicyclo[4.3.0]non-5-ene | 2,2-Dimethylnonanoic acid | 1.09 [8.05] | 1.77 [5.37] | 23.89[3] | 8 | (α, α')**2 | 5'00" |
| Example 18 | 1,8-Diazabicyclo[5.4.0]undec-7-ene | 2,2-Dimethylhexanoic acid | 1.45 [6.57] | 1.37 [6.93] | 24.33[3] | 5 | (α, α')**2 | 5'30" |
| Example 19 | 1,8-Diazabicyclo[5.4.0]undec-7-ene | 1-Methyl-1-cyclohexanecarboxylic acid | 1.45 [6.57] | 1.35 [7.03] | 24.33[3] | 6 | (α, α')**2 | 6'00" |
| Example 20 | 1,8-Diazabicyclo[5.4.0]undec-7-ene | 2-Methylhexanoic acid | 1.45 [6.57] | 1.24 [7.68] | 24.33[3] | 5 | (α, α')**1 | 6'00" |
| Example 21 | 1,8-Diazabicyclo[5.4.0]undec-7-ene | 2,2-Dimethylbutyric acid | 1.45 [6.57] | 1.10 [8.61] | 24.33[3] | 3 | (α, α')**2 | 6'30" |
| Example 22 | 1,8-Diazabicyclo[5.4.0]undec-7-ene | 2,2-Dimethylvaleric acid | 1.45 [6.57] | 1.24 [7.68] | 24.33[3] | 4 | (α, α')**2 | 6'30" |
| Example 23 | 1,8-Diazabicyclo[5.4.0]undec-7-ene | 2-Ethylhexanoic acid | 1.45 [6.57] | 1.37 [6.93] | 24.33[3] | 5 | (α)**1 | 7'00" |
| Example 24 | 1,8-Diazabicyclo[5.4.0]undec-7-ene | 2-Butyloctanoic acid | 1.45 [6.57] | 1.90 [4.99] | 24.33[3] | 7 | (α)**1 | 7'00" |
| Example 25 | 1,8-Diazabicyclo[5.4.0]undec-7-ene | 2-Ethylbutyric acid | 1.45 [6.57] | 1.10 [8.61] | 24.33[3] | 3 | (α)**1 | 7'00" |
| Example 26 | 1,8-Diazabicyclo[5.4.0]undec-7-ene | 2-Hexyldecanoic acid | 1.45 [6.57] | 2.44 [3.90] | 24.33[3] | 9 | (α)**1 | 7'00" |
| Example 27 | 1,8-Diazabicyclo[5.4.0]undec-7-ene | 2-Methylbutyric acid | 1.45 [6.57] | 0.97 [9.79] | 24.33[3] | 3 | (α)**1 | 7'30" |
| Example 28 | 1,8-Diazabicyclo[5.4.0]undec-7-ene | Pivalic acid | 1.45 [6.57] | 0.97 [9.79] | 24.33[3] | 2 | (α, α')**2 | 7'30" |
| Example 29 | 1,8-Diazabicyclo[5.4.0]undec-7-ene | Decanoic acid | 1.45 [6.57] | 1.64 [5.80] | 24.33[3] | 9 | 0 | 8'00" |
| Example 30 | 1,8-Diazabicyclo[5.4.0]undec-7-ene | 4-Methylhexanoic acid | 1.45 [6.57] | 1.24 [7.68] | 24.33[3] | 5 | (γ)**1 | 8'00" |
| Example 31 | 1,8-Diazabicyclo[5.4.0]undec-7-ene | Octanoic acid | 1.45 [6.57] | 1.37 [6.93] | 24.33[3] | 7 | 0 | 8'00" |
| Example 32 | 1,8-Diazabicyclo[5.4.0]undec-7-ene | Hexanoic acid | 1.45 [6.57] | 1.10 [8.61] | 24.33[3] | 5 | 0 | 8'00" |
| Example 33 | 1,8-Diazabicyclo[5.4.0]undec-7-ene | Bicyclo[2.2.1]-5-heptan-2-carboxylic acid | 1.45 [6.57] | 1.33 [6.57] | 24.33[3] | 6 | 2 | 8'00" |
| Example 34 | 1,8-Diazabicyclo[5.4.0]undec-7-ene | Myristic acid | 1.45 [6.57] | 2.17 [4.38] | 24.33[3] | 13 | 0 | 8'00" |
| Example 35 | 1,8-Diazabicyclo[5.4.0]undec-7-ene | 2-Propylpentanoic acid | 1.45 [6.57] | 1.37 [6.93] | 24.33[3] | 4 | (α)**1 | 8'30" |
| Example 36 | 1,8-Diazabicyclo[5.4.0]undec-7-ene | Enanthic acid | 1.45 [6.57] | 1.24 [7.69] | 24.33[3] | 6 | 0 | 9'00" |
| Example 37 | 1,8-Diazabicyclo[5.4.0]undec-7-ene | Cyclohexanecarboxylic acid | 1.45 [6.57] | 1.22 [7.80] | 24.33[3] | 6 | (α, α')**2 | 9'00" |
| Example 38 | 1,8-Diazabicyclo[5.4.0]undec-7-ene | Isobutyric acid | 1.45 [6.57] | 0.84 [11.35] | 24.33[3] | 3 | (β)**1 | 9'30" |
| Example 39 | 1,8-Diazabicyclo[5.4.0]undec-7-ene | Oleic acid | 1.45 [6.57] | 2.68 [3.54] | 24.33[3] | 15 | 0 | 10'30" |
| Example 40 | 1,8-Diazabicyclo[5.4.0]undec-7-ene | Stearic acid (octadecanoic | 1.45 [6.57] | 2.70 [3.52] | 24.33[3] | 17 | 0 | 10'30" 10'30" |
| Comparison Example 8 | 1,8-Diazabicyclo[5.4.0]undec-7-ene | Hydrochloric acid | 1.45 [6.57] | 0.35 [27.43] | 24.33[3] | —* | —* | >30 min. |
| Comparison Example 9 | 1,8-Diazabicyclo[5.4.0]undec-7-ene | Benzoic acid | 1.45 [6.57] | 1.16 [8.19] | 24.33[3] | 6 | 1 | >30 min. |
| Comparison Example 10 | 1,8-Diazabicyclo[5.4.0]undec-7-ene | Acetic acid | 1.45 [6.57] | 0.57 [16.65] | 24.33[3] | 1 | 0 | >30 min. |
| Comparison Example 11 | 1,8-Diazabicyclo[5.4.0]undec-7-ene | Acrylic acid | 1.45 [6.57] | 0.68 [13.88] | 24.33[3] | 2 | 0 | >30 min. |
| Comparison Example 12 | 1,8-Diazabicyclo[5.4.0]undec-7-ene | Formic acid | 1.45 [6.57] | 1.44 [21.72] | 24.33[3] | 0 | — | >60 min. |
| Comparison Example 13 | 1,8-Diazabicyclo[5.4.0]undec-7-ene | Salicylic acid | 1.45 [6.57] | 1.31 [7.24] | 24.33[3] | 6 | 1 | No reaction |

TABLE 2-continued

Composition and binding time of the compositions according to Examples 13 to 40 and Comparison Examples 8 to 19

| Example pursuant to the invention/ Comparison Example | Strong base | Weak acid | Base (%) [mmol/g] | Acid (%) [mmol/g] | Number pK$_{BH+}$ Base (MeCN) | Number of Substituents in of C atoms of longest C chain | Number of the longest C chain of the acid[2] | Setting time |
|---|---|---|---|---|---|---|---|---|
| Comparison Example 14 | 1,8-Diazabicyclo[5.4.0]undec-7-ene | Acetylsalicylic acid | 1.45 [6.57] | 1.71 [5.55] | 24.33[3] | 6 | 1 | No reaction |
| Comparison Example 15 | 1,8-Diazabicyclo[5.4.0]undec-7-ene | Ascorbic acid | 1.45 [6.57] | 1.67 [5.68] | 24.33[3] | — | — | No reaction |
| Comparison Example 16 | 1,8-Diazabicyclo[5.4.0]undec-7-ene | Sulfuric acid | 1.45 [6.57] | 0.93 [10.20] | 24.33[3] | — | — | No reaction |
| Comparison Example 17 | 1,8-Diazabicyclo[5.4.0]undec-7-ene | Phosphoric acid | 1.45 [6.57] | 0.93 [10.21] | 24.33[3] | — | — | No reaction |
| Comparison Example 18 | 1,8-Diazabicyclo[5.4.0]undec-7-ene | o-Phthalic acid | 1.45 [6.57] | 1.58 [6.02] | 24.33[3] | 6 | 1 | No reaction |
| Comparison Example 19 | 1,8-Diazabicyclo[5.4.0]undec-7-ene | p-Toluenesulfonic acid | 1.45 [6.57] | 1.81 [5.26] | 24.33[3] | — | — | No reaction |

[2]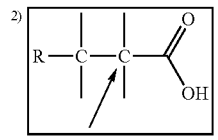

Carbon in the position alpha to the carboxyl group
[3]Source: Sigma-Aldrich, ChemFiles Vol. 3, No. 1
*without carboxyl group
**in position to the carboxyl group

TABLE 3

Processing and setting times and stabilities of dental materials based on alkoxysilylpolyethers compared with Example 3 and 5 of EP 1226808 A2

| Impression material | Processing time[1] | Setting time[2] | Stability: Setting time after one week at 60° C.[3] |
|---|---|---|---|
| Example 9 | 2.00 min | 7.00 min | 7.00 min |
| Comparison Example 20 | 0.50 min | 5.00 | >15.00 min |
| Examples 3 and 5 EP 122 6808 A2 | | | |

[1]According to ISO 4823 (1992 version)
[2]Determined through recovery after deformation according to ISO 4823 (1992 version)
[3]Stored in sealed foil bags made of PE/Al/PE composite film; see under [2] for measurement

TABLE 4

Examples pursuant to the invention for astringent and/or antibacterial additives according to Example 9

| Example | Astringent or antibacterial additive | Amount added (parts) | Setting time [min] | Stability Setting time after 1 week at 60° C. [min] |
|---|---|---|---|---|
| 9a | None | 0.0 | 7.00 | 7.00 |
| 9b | Triclosan | 0.6 | 7.00 | 7.00 |
| 9c | Epinephrine | 0.6 | 7.00 | 7.00 |
| 9d | Chlorhexidine | 0.6 | 7.50 | 7.50 |
| 9e | Hexetidine | 0.6 | 7.25 | 7.75 |

TABLE 5

Applied properties of the compositions pursuant to Examples 9 and 9c

| | Example 9 | Example 9c Epinephrine added |
|---|---|---|
| Consistency[1] of catalyst component B | 39 mm | 38 mm |
| Consistency[2] of base component A | 35 mm | 35 mm |
| Consistency of mixture[2] | 36 mm | 36 mm |
| Linear dimensional change[3] | −0.45% | −0.45% |
| Shore A hardness immediately after completion of setting[4] | 56 | 54 |
| Shore A hardness immediately after 15 hours of storage[4] | 63 | 63 |
| Contact angle[5] | 40 | 40 |
| Recovery after deformation[6] | 98.9% | 98.6% |

[1]From ISO 4823, consistency of mixture, load weight 500 g, load time 15 s
[2]From ISO 4823, consistency of mixture, load weight 1500 g, load time 5 s
[3]According to ISO 4823
[4]According to DIN 53505 with digital Shore A hardness tester, Zwick Co.
[5]Measured by the sessile drop method, contact angle measurement system G40 from the Krüss Co., initial contact angle (age of test specimen: apply the drop 45 sec after beginning to mix), measurement time: 30 sec after application of the drop, use of demineralized water.
[6]According to ISO 4823.

TABLE 6

Setting time of the composition pursuant to Example 41

| Example | Crown ether-alkali metal complex cation | Anion of weak acid | (%) Crown ether complex [mmol/g] | (%) Anion of weak acid [mmol/g] | Setting time |
|---|---|---|---|---|---|
| Example 41 | 18-Crown-6-potassium | 2-Ethyl- | 2.88 [3.30] | 1.37 [6.93] | 7'00" |

TABLE 6-continued

Setting time of the composition pursuant to Example 41

| Example | Crown ether-alkali metal complex cation | Anion of weak acid | (%) Crown ether complex [mmol/g] | (%) Anion of weak acid [mmol/g] | Setting time |
|---|---|---|---|---|---|
| | complex cation | hexanoate anion | | | |

The invention claimed is:

1. Condensation-crosslinking two-component dental material with a component A containing
   a) at least one alkoxysilyl-functional polyether which comprises besides the terminal alkoxy groups and the polyether groups a third structural unit of alkylene spacers, each located on the terminal alkoxysilyl groups, and as a fourth structural unit at least one of urethane groups and urea groups, wherein the individual structural units of the at least one polyether a) are arranged according to at least one of

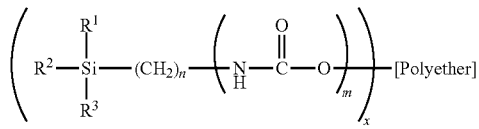

wherein $R^1$, $R^2$, and $R^3$ independently of one another are alkoxy, alkyl, aryl, aralkyl, alkylaryl groups, or hydrogen, provided that at least one of the aforementioned residues is an alkoxy group, and
x=1 to 6,
n=1 to 6, and
m=1,
and

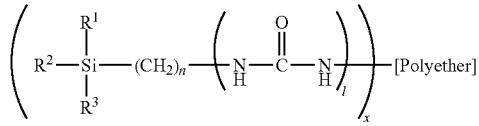

wherein $R^1$, $R^2$, and $R^3$ independently of one another are alkoxy, alkyl, aryl, aralkyl, alkylaryl groups, or hydrogen, provided that at least one of the aforementioned residues is an alkoxy group, and
x=1 to 6,
n=1 to 6, and
l=1,
and a component B containing
   b) at least one catalyst and
   c) water,
wherein the at least one catalyst b) is a salt that is formed from at least one cation selected from cations formed by protonation of a base with a $pK_{BH+}$ value of at least 21 measured in acetonitrile,
wherein the base has at least one structural unit according to the general formula I

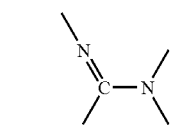

and/or according to the general formula II

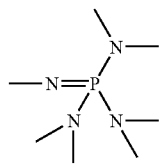

and/or according to the general formula III

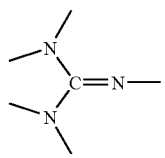

and at least one anion of branched carboxylic acid with a length of the (cyclo)alkyl chain provided on the carboxyl group of at least 3 carbon atoms, or an unbranched carboxylic acid with a length of the (cyclo)alkyl chain provided on the carboxyl group of at least 5 carbon atoms, wherein the dental material has a maximum setting time in a patient's mouth of 10 minutes as determined according to ISO 4823, 1992 version.

2. Condensation-crosslinking two-component dental material pursuant to claim 1, wherein it contains in component A and/or in component B at least one reinforcing filler $d_1$) with a BET surface area of at least 50 m$^2$/g and/or at least one non-reinforcing filler $d_2$) with a BET surface area of less than 50 m$^2$/g.

3. Dental material pursuant to claim 1, wherein the cation used for the catalyst salt b) is a protonated base selected from the group consisting of 1,1,3,3-tetramethylguanidine, diazabicyclo[5.4.0]undec-7-ene, 1,5-diazabicyclo[4.3.0]non-5-ene, tert-butyliminotris(dimethylamino)phosphorane, tert-butyliminotri(pyrrolidino)phosphorane, tert-octyliminotris(dimethylamino)phosphorane, 2-tert-butylimino-2-diethylamino-1,3-dimethylperhydro-1,3,2-diazaphosphorine, 2-tert-butylimino-2-diethylamino-1,3-dimethylperhydro-1,3,2-diazaphosphorine on polystyrene, 1-tert-butyl-2,2,4,4,4-pentakis(diethylamino)-2Λ5,4Λ5-catenadi(phosphazene), 1-ethyl-2,2,4,4,4-pentakis(diethylamino)-2Λ5,4Λ5-catenadi(phosphazene), 1-tert-butyl-4,4,4-tris(dimethylamino)-2,2-bis[tris(dimethylamino)phosphoranyliden-amino]-2Λ5,4Λ5-catenadi(phosphazene), 1-tert-octyl-4,4,4-tris(dimethylamino)-2,2-bis[tris(dimethylamino)phosphoranylidenamino]-2Λ5,4Λ5-catenadi(phosphazene), 2,8,9-triisobutyl-2,5,8,9-tetraaza-1-phosphabicyclo[3.3.3]undecane, 2,8,9-triisopropyl-2,5,8,9-tetraaza-1-phosphabicyclo[3.3.3]undecane, 2,8,9-trimethyl-2,5,8,9-tetraaza-1-phosphabicyclo[3.3.3]undecane, 1,8-bis(tetramethylguanidino)naphthalene, 2-tert-butyl-1,1,3,3-tetramethylguanidine, 1,5,7-triazabicyclo(4.4.0)dec-5-ene, 7-methyl-1,5,7-triazabicyclo(4.4.0)dec-5-ene, 1,5-diazabicyclo(4.3.0)dec-5-ene, and 3,3,6,9,9-pentamethyl-2,10-diazabicyclo(4.4.0)dec-1-ene.

4. Dental material pursuant to claim 1, wherein the at least one anion of the catlyst salt b) is a branched carboxylic acid with a length of the (cyclo)alkyl chain provided on the carboxyl group of at least 3 carbon atoms, and wherein the (cyclo)alkyl chain has at least one branch in the γ-position relative to the carboxyl group.

5. Dental material pursuant to claim 1, wherein the anion of the catalyst salt b) is an ion selected from the group consisting of deprotonated 2,2-dialkylalkanoic acids, 3,3-dialkylalkanoic acids, 4,4-dialkylalkanoic acids, 2,3-dialkylalkanoic acids, 2,4-dialkylalkanoic acids, 3,4-dialkylalkanoic acids, 2,2-dialkylalkenoic acids, 3,3-dialkylalkenoic acids, 4,4-dialkylalkenoic acid, 2,3-dialkylalkenoic acids, 2,4-dialkylalkenoic acids, 3,4-dialkylalkenoic acids, 2,2-dialkylalkynoic acids, 3,3-dialkylalkynoic acids, 4,4-dialkylalkynoic acids, 2,3-dialkylalkynoic acids, 2,4-dialkylalkynoic acids, 3,4-dialkylalkynoic acids, 2-monoalkylalkanoic acids, 3-monoalkylalkanoic acids, 4-monoalkylalkanoic acids, 2,2-dialkylhexanoic acids.

6. Dental material pursuant to claim 1, wherein based on the total mixture, it contains at least one catalyst b) in the amount of 0.001 to 1 mmol/g.

7. Dental material pursuant to claim 1, wherein it contains no other catalyst besides one or more salts according to claim 2.

8. Dental material pursuant to claim 1, wherein the fourth structural unit has 0.02 to 8 mmol/g of at least one of urethane groups and urea groups.

9. Dental material pursuant to claim 2, wherein n is equal to 1.

10. Dental material pursuant to claim 1, wherein it contains at least one water scavenger g).

11. Dental material pursuant to claim 1, wherein it contains at least one paste-former h).

12. Mixture obtained by mixing components A and B of the two-component dental material pursuant to claim 1, wherein the base component A is mixed with the catalyst component B in a ratio of 1:1 to 20:1.

13. Condensation-crosslinking dental material pursuant to claim 1, wherein the cation used for the catalyst salt b) is a protonated base selected from the group consisting of 1,1,3,3-tetramethylguanidine , diazabicyclo[5.4.0]undec-7-ene, 1,5-diazabicyclo[4.3.0]non-5-ene, tert-butyliminotris(dimethylamino)phosphorane, tert-butyliminotri(pyrrolidino)phosphorane, tert-octyliminotris(dimethylamino)phosphorane, 2-tert-butylimino-2-diethylamino-1,3-dimethylperhydro-1,3,2-diazaphosphorine, 2-tert-butylimino-2-diethylamino-1,3-dimethylperhydro-1,3,2-diazaphosphorine on polystyrene, 1-tert-butyl-2,2,4,4,4-pentakis(diethylamino)-2$\Lambda$5, 4$\Lambda$5-catenadi(phosphazene), 1-ethyl-2,2,4,4,4-pentakis(diethylamino)-2$\Lambda$5, 4$\Lambda$5-catenadi(phosphazene), 1-tert-butyl-4,4,4-tris(dimethylamino)-2,2-bis[tris(dimethylamino)phosphoranyliden-amino]-2$\Lambda^5$, 4$\Lambda^5$-catenadi(phosphazene), 1-tert-octyl-4,4,4-tris(dimethylamino)-2,2-bis[tris (dimethylamino) phosphoranylidenamino]-2$\Lambda^5$,4$\Lambda^5$-catenadi (phosphazene), 2,8,9-triisobutyl-2,5,8,9-tetraaza-1-phosphabicyclo[3.3.3]undecane, 2,8,9-triisopropyl-2,5,8,9-tetraaza-1-phosphabicyclo[3.3.3]undecane, 2,8,9-trimethyl-2,5,8,9-tetraaza-1-phosphabicyclo[3.3.3] undecane, 1,8-bis(tetramethylguanidino)naphthalene, 2-tert-butyl-1,1,3,3-tetramethylguanidine, 1,5,7-triazabicyclo(4.4.0)dec-5-ene, 7-methyl-1,5,7-triazabicyclo (4.4.0)dec-5-ene, 1,5-diazabicyclo(4.3.0)dec-5-ene, and 3,3,6,9,9-pentamethyl-2,10-diazabicyclo(4.4.0) dec-1-ene;

wherein the at least one anion of the catalyst salt b) is an ion selected from the group consisting of deprotonated 2,2-dialkylalkanoic acids, 3,3-dialkylalkanoic acids, 4,4-dialkylalkanoic acids, 2,3-dialkylalkanoic acids, 2,4-dialkylalkanoic acids, 3,4-dialkylalkanoic acids, 2,2-dialkylalkenoic acids, 3,3-dialkylalkenoic acids, 4,4-dialkylalkenoic acid, 2,3-dialkylalkenoic acids, 2,4-dialkylalkenoic acids, 3,4-dialkylalkenoic acids, 2,2-dialkylalkynoic acids, 3,3-dialkylalkynoic acids, 4,4-dialkylalkynoic acids, 2,3-dialkylalkynoic acids, 2,4-dialkylalkynoic acids, 3,4-dialkylalkynoic acids, 2-monoalkylalkanoic acids, 3-monoalkylalkanoic acids, 4-monoalkylalkanoic acids, 2,2-dialkylhexanoic acids; and wherein the at least one polyether a) has a third structural unit of alkylene spacers, each located on the terminal alkoxysilyl groups, and as a fourth structural unit has 0 to 8 mmol/g of at least one of urethane groups and urea groups.

* * * * *